(12) United States Patent
Itani

(10) Patent No.: US 8,740,799 B2
(45) Date of Patent: Jun. 3, 2014

(54) ULTRASOUND DIAGNOSTIC APPARATUS

(75) Inventor: Kazunori Itani, Tokyo (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 857 days.

(21) Appl. No.: 12/480,924

(22) Filed: Jun. 9, 2009

(65) Prior Publication Data
US 2010/0036255 A1 Feb. 11, 2010

(30) Foreign Application Priority Data

Aug. 8, 2008 (JP) ................................. 2008-206046

(51) Int. Cl.
*A61B 8/14* (2006.01)
*A61B 8/08* (2006.01)

(52) U.S. Cl.
CPC .. *A61B 8/481* (2013.01); *A61B 8/14* (2013.01)
USPC .......................................... 600/458; 600/437

(58) Field of Classification Search
None
See application file for complete search history.

(56) References Cited

U.S. PATENT DOCUMENTS

| | | | | |
|---|---|---|---|---|
| 5,469,849 | A * | 11/1995 | Sasaki et al. | 600/443 |
| 5,902,243 | A * | 5/1999 | Holley et al. | 600/443 |
| 5,947,904 | A * | 9/1999 | Hossack et al. | 600/458 |
| 6,095,980 | A | 8/2000 | Burns et al. | |
| 6,117,082 | A | 9/2000 | Bradley et al. | |
| 6,193,663 | B1 * | 2/2001 | Napolitano et al. | 600/447 |
| 6,213,947 | B1 * | 4/2001 | Phillips | 600/443 |
| 6,371,917 | B1 * | 4/2002 | Ferrara et al. | 600/458 |
| 6,423,007 | B2 * | 7/2002 | Lizzi et al. | 600/458 |
| 6,440,075 | B1 | 8/2002 | Averkiou | |
| 6,450,961 | B1 * | 9/2002 | Shiki et al. | 600/458 |
| 6,626,836 | B2 * | 9/2003 | Mao et al. | 600/455 |
| 6,632,177 | B1 * | 10/2003 | Phillips et al. | 600/458 |
| 6,896,659 | B2 * | 5/2005 | Conston et al. | 600/458 |
| 6,899,681 | B1 * | 5/2005 | Phillips et al. | 600/458 |

(Continued)

FOREIGN PATENT DOCUMENTS

| | | |
|---|---|---|
| EP | 1406096 A1 | 4/2004 |
| EP | 1739455 A1 | 1/2007 |

(Continued)

OTHER PUBLICATIONS

Notice of Grounds for Rejection dated Aug. 10, 2010, issued in corresponding Japanese Patent Application No. 2008-206046.

(Continued)

*Primary Examiner* — Long V. Le
*Assistant Examiner* — Bradley Impink
(74) *Attorney, Agent, or Firm* — Westerman, Hattori, Daniels & Adrian, LLP

(57) ABSTRACT

A signal generation unit 10 generates, and sends to a transmission circuit 12, a driving signal for forming a transmission pulse. A probe 14 is transmission controlled to transmit ultrasound at a transmission frequency which is set using, as a reference, a resonance frequency of a bubble administered into a living organism, and also at a transmission sound pressure which is set using an expansion ratio of the bubble as a reference. The signal generation unit 10 outputs a transmission pulse having a waveform corresponding to a center frequency of about 1.5 MHz and a transmission sound pressure of about 200 to 300 kPa. With this structure, it is possible to increase a harmonic component obtained from the bubble while suppressing a harmonic component obtained from real tissue, so that extremely high CTR can be obtained.

12 Claims, 19 Drawing Sheets

(56) References Cited

U.S. PATENT DOCUMENTS

| | | | |
|---|---|---|---|
| 6,953,434 B2 | 10/2005 | Hao et al. | |
| 7,591,788 B2 * | 9/2009 | Phillips et al. | 600/458 |
| 2001/0044278 A1 * | 11/2001 | Chiao et al. | 455/67.1 |
| 2007/0016051 A1 * | 1/2007 | Trucco et al. | 600/458 |

FOREIGN PATENT DOCUMENTS

| | | |
|---|---|---|
| JP | 11-178824 A | 7/1999 |
| JP | 2001-258882 A | 9/2001 |
| JP | 2004-113788 A | 4/2004 |
| JP | 2004-510514 T | 4/2004 |
| JP | 2004-208918 A | 7/2004 |
| JP | 2005-152177 A | 6/2005 |
| JP | 2006-217944 A | 8/2006 |
| JP | 2006-271599 A | 10/2006 |

OTHER PUBLICATIONS

Yang, Sun et al.; "Contrast Imaging with Chirped Excitation"; IEEE Transaction on Ultrasonics, Ferroelectrics and Frequency Control, Mar. 2007, vol. 54, Issue 3, pp. 520-529.

K. Itani et al., "Preparation and Detection of Nanobubbles: Toward Ultrasonic Molecular Imaging", Conferecnce presentation, Dec. 16, 2007.

Aloka Co., Ltd., "Health Relief Program; Research and Development Project of Molecular Imaging Devices; Research and Development Project of Molecular Imaging Devices for Supporting Treatment of Malignant Tumors; Leading Research related to Molecular Imaging Devices for Supporting Treatment of Malignant Tumors; and Leading Research related to Research and Development of Super-fast Diagnosis System of Cancer by Ultrasound using Labeling Contrast Agent", New Energy and Industrial Technology Development Organization, Mar. 2008.

European Search Report dated Nov. 20, 2009, issued in corresponding European Patent Application No. 09007493.1.

Chiao, R. Y. et al.; "Coded Excitation for Diagnostic Ultrasound: A System Developer's Perspective"; 2003 IEEE Ultrasonics Symposium Proceedings, Oct. 2003,vol. 1-5 , pp. 437-448, XP010702942.

Simpson, David Hope et al; "Pulse Inversion Doppler: A New Method for Detecting Nonlinear Echoes from Microbubble Contrast Agents"; IEEE Transactions on Ultrasonics, Ferroelectrics and Frequency Control, IEEE, Mar. 1, 1999, vol. 46, No. 2, pp. 372-382, XP010702942.

Chetty, David et al; "Investigating the Nonlinear Microbubble Response to Chirp Encoded, Multipulse Sequences"; Ultrasound in Medicine and Biology, Dec. 2006, vol. 32, No. 12, pp. 1887-1895, XP005801996.

Borsboom, J. M. G. et al; "Harmonic Chirp Imaging Method for Ultrasound Contrast Agent"; IEEE Transactions on Ultrasonics, Ferroelectrics and Frequency Control, Feb. 2005, vol. 52, No. 2, pp. 241-249, XP00235077.

Borsboom, J. M. G .et al; "Nonlinear Coded Excitation Method for Ultrasound Contrast Imaging"; Ultrasound in Medicine and Biology, Feb. 2003, vol. 29, No. 2, pp. 277-284, XP004416965.

Chinese Office Action dated Oct. 30, 2012, issued in corresponding Chinese Patent Application No. 2012102500914960, with English translation (10 pages).

Office Action dated Apr. 12, 2012 and issued in corresponding Chinese Patent Application 200910146033.6. English Translation.

* cited by examiner

| | | BUBBLE SIGNAL | TISSUE SIGNAL AMOUNT | CONTRAST TO TISSUE RATIO CRT=C/T | CTR RELATIVE TO PI TECHNOLOGY | PULSE WIDTH |
|---|---|---|---|---|---|---|
| NORMAL PI TECHNOLOGY | | 1 | 1 | 1 | 0 | 1 |
| PRESENT EMBODIMENT | SECOND ALONE | 0.74 | 1.55 | 0.47 | -6.6 | 1 |
| | THIRD ALONE | 1.3 | 0.17 | 7.64 | 17.7 | 0.75 |
| | FOURTH ALONE | 1.74 | 0.022 | 79.1 | 37.9 | 0.5 |
| | FIFTH ALONE | 1.86 | 0.0028 | 664 | 56.4 | 0.4 |
| | FOURTH + FIFTH | 3.51 | 0.025 | 140 | 42.9 | 0.22 |
| | THIRD TO FIFTH | 4.84 | 0.27 | 17.9 | 25.1 | 0.18 |
| | SECOND TO FIFTH | 5.57 | 1.75 | 3.18 | 10.0 | 0.17 |

FIG. 18

ULTRASOUND DIAGNOSTIC APPARATUS

BACKGROUND

1. Technical Field

The present invention relates to an ultrasound diagnostic apparatus, and more particularly to image forming technology in which bubbles are used.

2. Related Art

Microbubbles (nanobubbles) as used herein refer to fine air bubbles injected into a liquid and so on. Due to various excellent characteristics, microbubbles are being utilized in many technical fields. In application to the medical field, for example, microbubbles, which can serve as a preferable reflector of ultrasound, are being utilized as a contrast agent for forming an ultrasound image.

In ultrasound image formation using a contrast agent, technologies in which a harmonic component obtained from bubbles is focused are known, of which phase inversion technology (a pulse inversion technology) and power modulation technology are especially well known. Obviously, there exist a large number of technical documents concerning the image forming technology focusing on the harmonic components, including JP 2005-152177 A (Patent Document 1), JP 2001-258882 A (Patent Document 2), and JP 2006-271559 A (Patent Document 3), for example. Here, it should be noted that neither Patent Document 1 nor 2 describes the technology in which three-dimensional harmonics obtained from bubbles are positively imaged. Further, Patent Document 3 describes landmark technology in which the principle of the phase inversion technology is applied to form an image of a harmonic component by using two transmission signals having phases that are inverted with respect to each other.

In the case of forming an image of microbubbles (a contrast agent) which are injected into a relatively thick blood vessel and so on, it is possible to achieve a relatively high contrast by using conventionally known technology, because blood, in which scattering of ultrasound or the like is unlikely to be observed, is present around the microbubbles. On the contrary, when observing microbubbles surrounded by a capillary and a lymph node such as tissue and a tumor, because real tissue is present around the microbubbles, it is more difficult to achieve a high contrast than when blood exists around the microbubbles.

Further, a contrast agent suitable for imaging using ultrasound at a low-middle sound pressure (e.g. "Sonazoid" (registered mark)) has recently drawn attention, and highly sensitive imaging technology using ultrasound at a low-middle sound pressure is also desired.

Under such circumstances, the present inventors have continued to research and improve imaging technology by ultrasound in which bubbles (e.g., microbubbles) are utilized, particularly the behavior of bubbles to which ultrasound has been applied. The present inventors have also continued to research and improve technology of extracting a harmonic component obtained from a target subject such as bubbles.

SUMMARY

The present invention was made in the course of the above researches, and advantageously provides appropriate image processing technology based on the behavior of bubbles. The present invention also advantageously increases a precision of extraction of a harmonic component obtained from a target subject.

In order to attain the above advantages, in one aspect of the invention, an ultrasound diagnostic apparatus includes a probe that transmits and receives ultrasound with respect to a diagnostic region including a bubble; a transmission control unit that controls the probe to transmit ultrasound under transmission conditions which are set based on structural characteristics of a bubble; a reception processing unit that obtains a reception signal corresponding to ultrasound received by the probe; a harmonic extraction unit that processes the reception signal to extract a harmonic component contained in the reception signal; and an image forming unit that forms image data concerning the bubble based on the harmonic component.

In the above aspect, because the transmission conditions of ultrasound are set based on the structural characteristics of a bubble, it is possible, for example, to increase a harmonic component obtained from the bubble and simultaneously suppress a harmonic component obtained from real tissue, so that an extremely high CTR (Contrast to Tissue Ratio), for example, can be obtained.

In a preferred aspect, the transmission control unit controls the probe to transmit ultrasound corresponding to each of a first transmission signal and a second transmission signal, phases of the first transmission signal and the second transmission signal being inverted with respect to each other, and the harmonic extraction unit extracts the harmonic component based on a first reception signal corresponding to the first transmission signal and a second reception signal corresponding to the second transmission signal.

In a preferred aspect, the transmission control unit controls the probe to transmit ultrasound corresponding to each of a first chirp signal and a second chirp signal, with phases of the first chirp signal and the second chirp signal being inverted with respect to each other, the reception processing unit obtains a first reception signal corresponding to the first chirp signal and a second reception signal corresponding to the second chirp signal, and the harmonic extraction unit extracts the harmonic component based on at least one of addition processing and subtraction processing performed between the first reception signal and the second reception signal, and the ultrasound diagnostic apparatus further includes a pulse compression processing unit that applies pulse compression processing to the harmonic component which is extracted.

In the above aspects, because the harmonic component of the reception signal is extracted based on at least one of the addition processing and the subtraction processing between the first reception signal and the second reception signal, it is possible to extract each harmonic component while suppressing mutual interference concerning the harmonic components of multiple orders, for example. It should be noted that in the above aspect, the first chirp signal and the second chirp signal having respective phases inverted with respect to each other are used. On the other hand, in the technology described in Patent Document 3, while a second transmission signal whose polarity is inverted with respect to that of a first transmission signal is used, chirp signals having polarities inverted with respect to each other are not used.

According to the present invention, appropriate image processing technology based on the behavior of bubbles can be provided. Further, according to the present invention, the precision of extracting a harmonic component obtained from a target subject can be increased.

BRIEF DESCRIPTION OF THE DRAWINGS

Preferred embodiments of the present invention will be described in detail by reference to the following figures, wherein:

FIG. 18 is a view illustrating a comparison result between the present embodiment and the normal PI method;

DETAILED DESCRIPTION

Preferred embodiments of the present invention will be described in detail with reference to the accompanying drawings.

Figure 1:
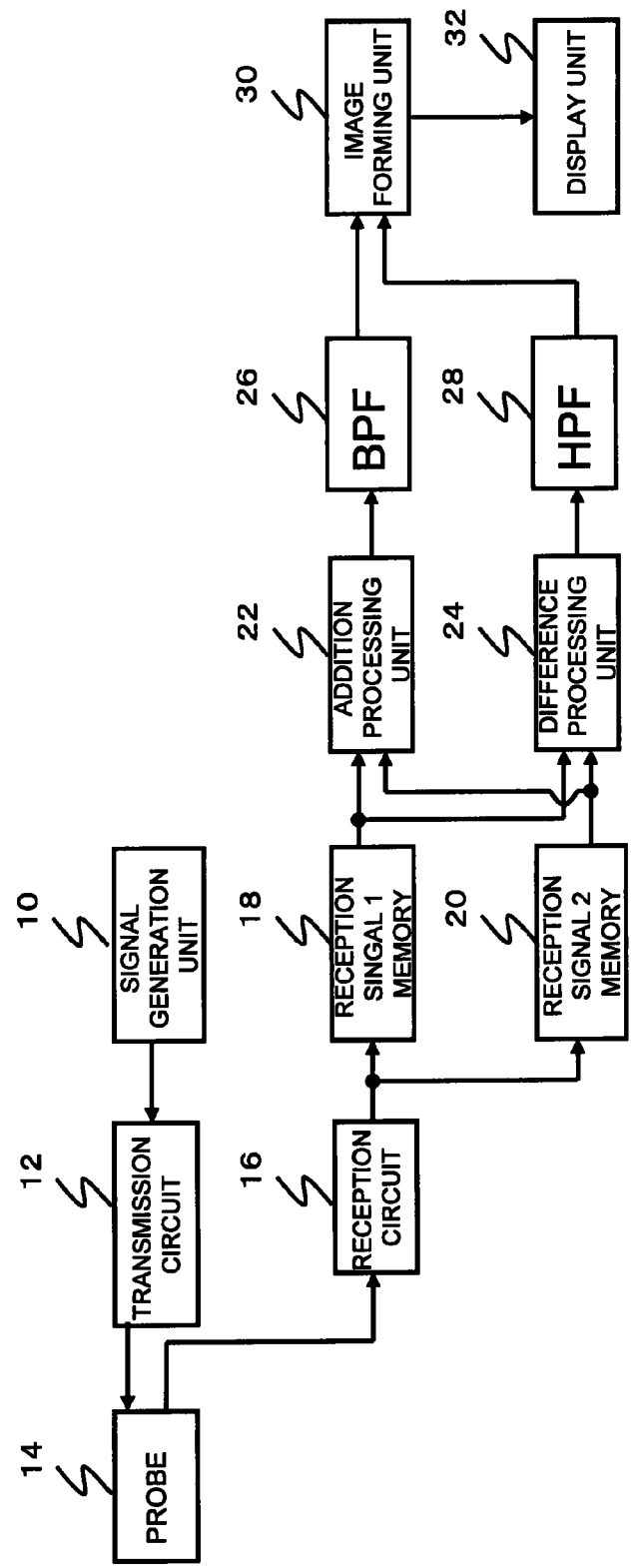
FIG. 1 is a block diagram illustrating a preferred embodiment of an ultrasound diagnostic apparatus according to the present invention.

FIG. 1 is a functional block diagram illustrating an overall structure of an ultrasound diagnostic apparatus according to a preferred embodiment of the present invention. The ultrasound diagnostic apparatus illustrated in FIG. 1 is suitable for forming an image by using a contrast agent including imaging bubbles (fine air bubbles such as microbubbles and nanobubbles).

While, in the present embodiment, it is desirable to use a contrast agent suitable for imaging by ultrasound of low-middle sound pressure (e.g. "Sonazoid" (registered mark)), for example, the contrast agent used in the present invention is not limited to any specific contrast agent. The contrast agent is administered to a diagnostic site within a living organism, such as a blood vessel or a tumor, for example. After elapse of a predetermined time from administration of the contrast agent until the bubbles are accumulated or captured within the living organism, diagnosis is carried out by using the ultrasound diagnostic apparatus illustrated in FIG. 1.

A signal generation unit 10 is controlled by a control unit which is not shown to generate a driving signal for forming a transmission pulse and output a transmission pulse to a transmission circuit 12. In the present embodiment, transmission control is performed such that ultrasound is transmitted at a transmission frequency which is set using, as a reference, a resonance frequency of bubbles administered in the living organism and also at a transmission sound pressure which is set using, as a reference, an expansion ratio of the bubbles. For example, the signal generation unit 10 outputs a transmission pulse having a waveform corresponding to a center frequency of approximately 1.5 MHz and a transmission sound pressure of approximately 200 to 300 kPa.

The transmission circuit 12 controls, based on the transmission pulse output from the signal generation unit 10, a plurality of transducer elements, which are not shown, provided in a probe 14, to form transmission beams and then to electronically scan the transmission beams thus formed, thereby forming a plurality of transmission beams over the entire region of the scanning region.

In the present embodiment, for each beam direction of the plurality of transmission beams, transmission is performed twice. More specifically, after first transmission is performed based on a transmission pulse with regard to one beam direction and a reception signal is obtained, second transmission follows, which is performed with regard to the same beam direction, based on a transmission pulse having the same waveform as that of the transmission pulse used in the first transmission and having a phase inverted with respect to the transmission pulse of the first transmission, and a reception signal is obtained. Then, after transmission is performed twice with regard to one beam direction, the beam direction is changed and further transmission is performed twice with regard to a new beam direction. In this manner, transmission is executed twice for each beam direction over the entire region of the scanning region.

The probe 14 transmits and receives ultrasound with respect to a diagnostic region within a living organism to which a contrast agent is administered. The probe 14 includes a plurality of transducer elements for transmitting and receiving ultrasound, and the plurality of transducer elements are controlled by the transmission circuit 12 to scan the transmission beams. Further, the plurality of transducer elements receive ultrasound reflected by the living organism and output signals obtained from the reflected waves to a reception circuit 16. Here, transmission and reception of ultrasound may be performed by different transducer elements.

The probe 14 has a frequency band including frequencies from a transmission frequency (having a center frequency of approximately 1.5 MHz, for example) to a frequency which is three times as high as the transmission frequency. Accordingly, assuming that the transmission frequency at the time of ultrasound transmission is the frequency of a fundamental wave, a reception signal containing components of the fundamental wave, a second harmonic, and a third harmonic can be obtained at the time of reception.

The reception circuit 16 applies phase alignment and summation processing to signals obtained from the plurality of transducer elements of the probe 14 to form a reception signal corresponding to each of a plurality of transmission beams within the scanning region. As transmission is performed twice for each beam direction of the plurality of transmission beams in the present embodiment, the reception circuit 16 forms, for each beam direction, a first reception signal corresponding to the first transmission and a second reception signal corresponding to the second transmission. Then, for each beam direction, the first reception signal (reception signal 1) is stored in a reception signal 1 memory 18 and the second reception signal (reception signal 2) is stored in a reception signal 2 memory 20.

An addition processing unit 22, for each beam direction, reads the reception signal 1 and the reception signal 2 from the reception signal 1 memory 18 and the reception signal 2 memory 20, respectively, and then adds the reception signal 1 and the reception signal 2. Because the reception signal 1 and the reception signal 2 are obtained from the transmission pulses having phases inverted with respect to each other, according to the principle of the phase inversion technology (or the pulse inversion technology), an odd-number order signal is cancelled and only an even-number order signal remains as a result of the addition processing of the reception signal 1 and the reception signal 2. More specifically, of the fundamental wave, the second harmonic, and the third harmonic contained in the reception signal, the fundamental wave and the third harmonic which are odd-number order signals are cancelled and the second harmonic signal which is an even-number order signal is extracted.

A bandpass filter (BPF) 26 is a filter having a pass-band corresponding to the second harmonic and removes noise or the like of the second harmonic so that only the second harmonic is extracted more reliably. Here, because, in principle, only the second harmonic can be reliably extracted by the addition processing unit 22, the bandpass filter 26 can be omitted.

A difference processing unit 24, for each beam direction, reads the reception signal 1 and the reception signal 2 from the reception signal 1 memory 18 and the reception signal 2 memory 20, respectively, and then computes a difference between the reception signal 1 and the reception signal 2. According to the principle of the phase inversion technology (or the pulse inversion technology), an even-number order signal is cancelled and only an odd-number order signal remains as a result of the difference processing of the reception signal 1 and the reception signal 2. More specifically, of the fundamental wave, the second harmonic, and the third harmonic contained in the reception signals, the even-number order second harmonic is cancelled and the fundamental wave and the third harmonic, which are odd-number order signals, are extracted.

A high pass filter (HPF) 28 is a filter having a pass-band corresponding to the third harmonic or higher order harmonics and removes the fundamental wave and noise or the like, so that only the third harmonic is extracted.

An image forming units 30 uses only the third harmonic obtained from the high pass filter 28 or also uses the second harmonic obtained from the bandpass filter 26 in addition to the third harmonic, to form image data of an ultrasound image. The image forming unit 30, based on the harmonic components (i.e. only the third harmonic, or the second harmonic and the third harmonic) obtained from each of the plurality of beam directions, forms image data of a two dimensional ultrasound image, for example. It is a matter of course that the ultrasound beam may be scanned in a three-dimensional manner to form image data of a three-dimensional ultrasound image. An ultrasound image corresponding to the image data formed in the image forming unit 30 is displayed on a display unit 32.

According to the present embodiment, as the transmission frequency is set using, as a reference, the resonance frequency of bubbles administered in the living organism and the transmission sound pressure is set using the expansion ratio of bubbles as a reference, it is possible, for example, to increase the harmonic components obtained from the bubbles while suppressing the harmonic components obtained from real tissue, so that an ultrasound image with an extremely high CTR (Contrast to Tissue Ratio) can be obtained.

The relationship between the transmission conditions or the like and the behavior of bubbles will be now described below. FIGS. 2 to 7 illustrate analysis results concerning the behavior of an ultrasound contrast agent (bubbles) by using a simulator which obtains vibration of a bubble membrane by means of numerical analysis.

Figure 2:
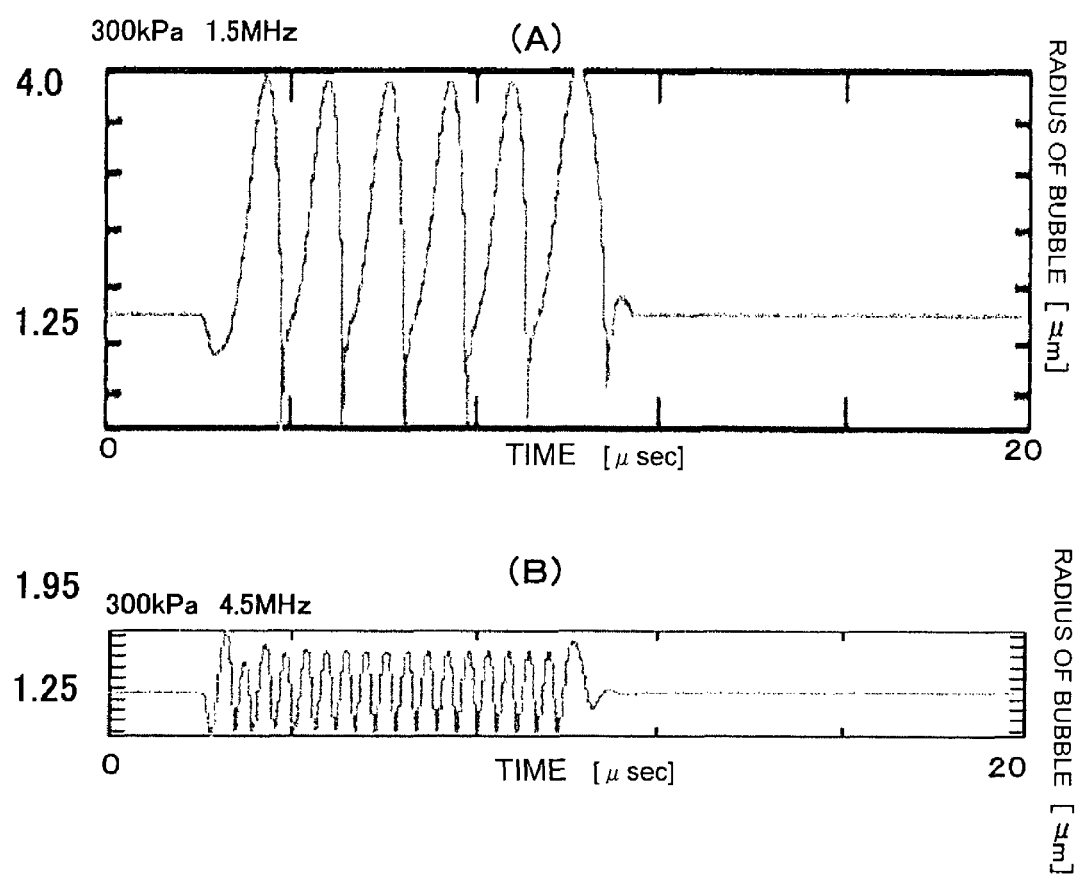
FIG. 2 is a view illustrating a simulation result of membrane vibration of bubbles.

FIG. 2 is a chart showing a simulation result of membrane vibration of bubbles. Specifically, FIG. 2(A) illustrates membrane vibration observed when ultrasound vibration with a transmission frequency (center frequency) of 1.5 MHz, a wave number of 6, and a sound pressure of 300 kPa was applied to bubbles having a radius of 1.25 μm, and FIG. 2(B) illustrates membrane vibration observed when ultrasound vibration with a transmission frequency (center frequency) of 4.5 MHz, a wave number of 18, and a sound pressure of 300 kPa was applied to the same bubbles. In both FIGS. 2(A) and 2(B), the vertical axis indicates a radius of a bubble, with the horizontal axis indicating time. Here, analysis was performed using the same conditions for the ultrasound energy (sound pressure×pulse length) which was applied to the bubbles in both FIGS. 2(A) and 2(B).

While bubbles expand threefold or more at the low frequency of 1.5 MHz as shown in FIG. 2(A), the expansion of bubbles is suppressed to 1.4 fold or less at the high frequency of 4.5 MHz as shown in FIG. 2(B). As the conditions of the bubbles, "Sonazoid (registered mark)" which is a commercially available contrast agent was assumed, the diameter of the bubble was 2.5 μm and the membrane thickness of the bubble was 3 nm. As other parameters of the bubbles, the conditions described in "Experimental and Theoretical Evaluation of Microbubble Behavior: IEEE Transaction on Ultrasonics, Ferroelectrics, and Frequency Control, Vol 47, No 6, November 2000" were used. The resonance frequency of the bubble under these conditions is approximately 2.5 MHz.

Figure 3:
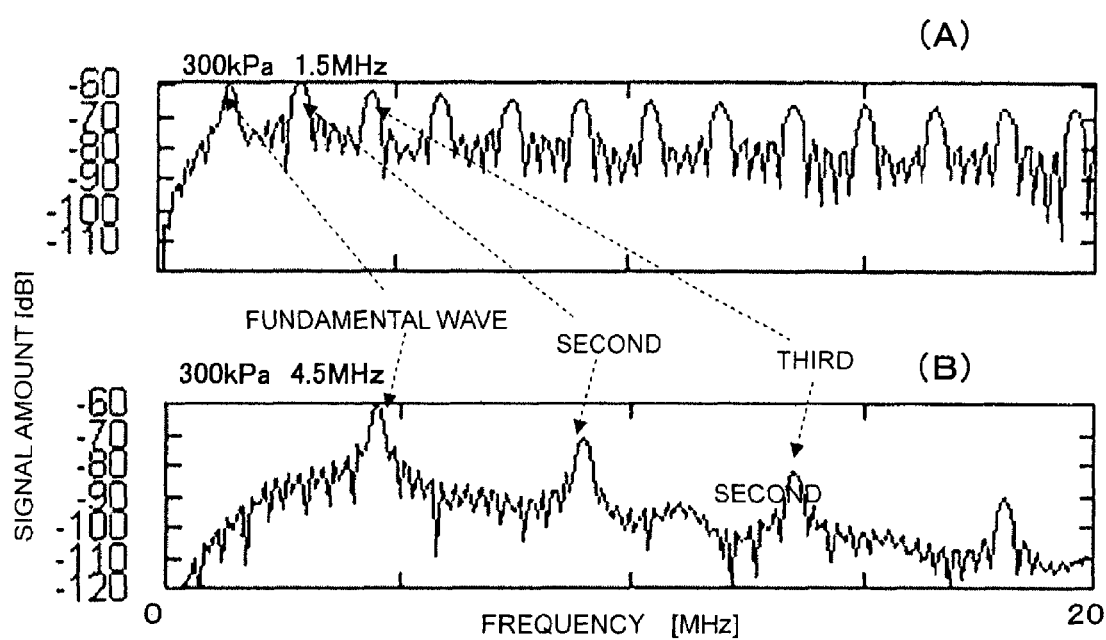
FIG. 3 is a view illustrating an ultrasound signal generated by membrane vibration of bubbles.

FIG. 3 shows a result of frequency analysis of an ultrasound signal generated by membrane vibration of the bubbles shown in FIG. 2. The analysis result of FIG. 3(A) corresponds to the membrane vibration shown in FIG. 2(A), and the analysis result of FIG. 3(B) corresponds to the membrane vibration shown in FIG. 2(B).

The signal amount of the fundamental wave is substantially the same at the frequency of 1.5 MHz in FIG. 3(A) and at the frequency of 4.5 MHz in FIG. 3(B). On the other hand, while at the frequency of 1.5 MHz the amount of the third harmonic remains substantially unchanged, i.e., −2 dB with respect to the fundamental wave, the amount of the third harmonic decreases considerably, i.e., −20 dB or more with respect to the fundamental wave, at the frequency of 4.5 MHz.

Figure 4:
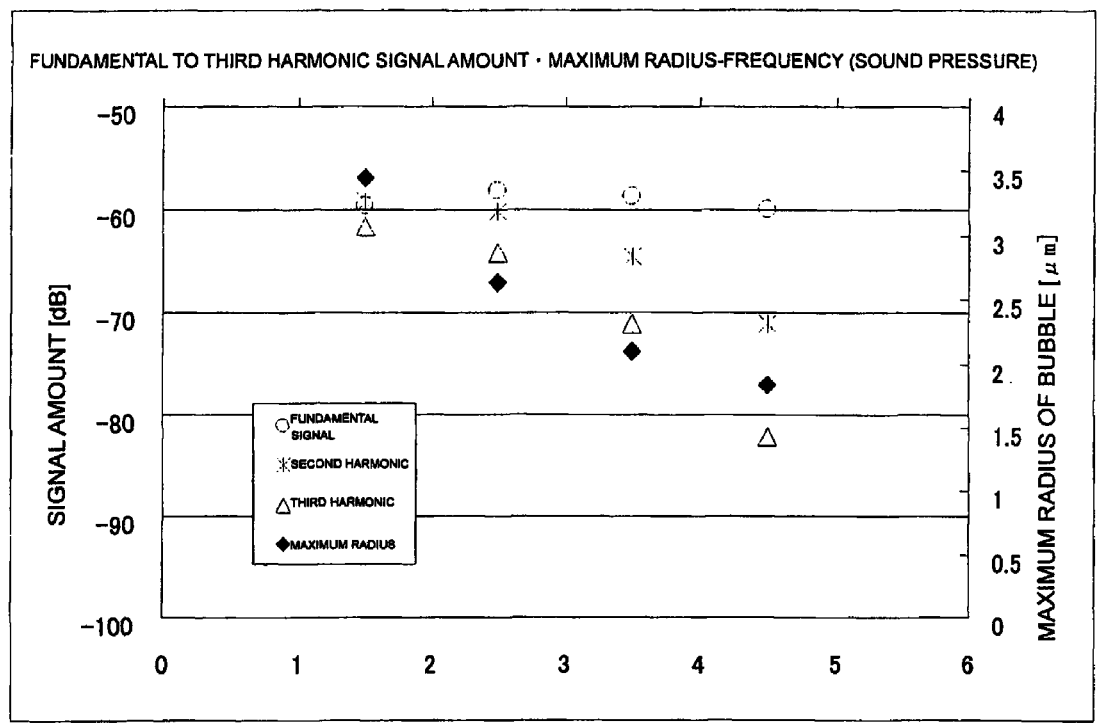
FIG. 4 is a view illustrating a correspondence relationship between a transmission frequency and a signal amount.

FIG. 4 shows a correspondence relationship between the transmission frequency and the signal amount. Specifically, FIG. 4 is a graph representing the analysis results of the bubble vibration maximum radius and the first harmonic (fundamental wave=transmission frequency), the second harmonic, and the third harmonic which were generated when vibration of a fixed signal amount (=sound pressure×time) was applied at the sound pressure of 300 kPa while varying the frequencies.

The bubbles vibrate more at a lower frequency. The signal amounts of ultrasound generated as a result of vibration do not vary considerably at various frequencies regarding the fundamental frequency (transmission frequency). However, with regard to the second and third harmonics, a signal with a higher intensity can be obtained in the case of ultrasound transmission at lower frequencies.

Figure 5:
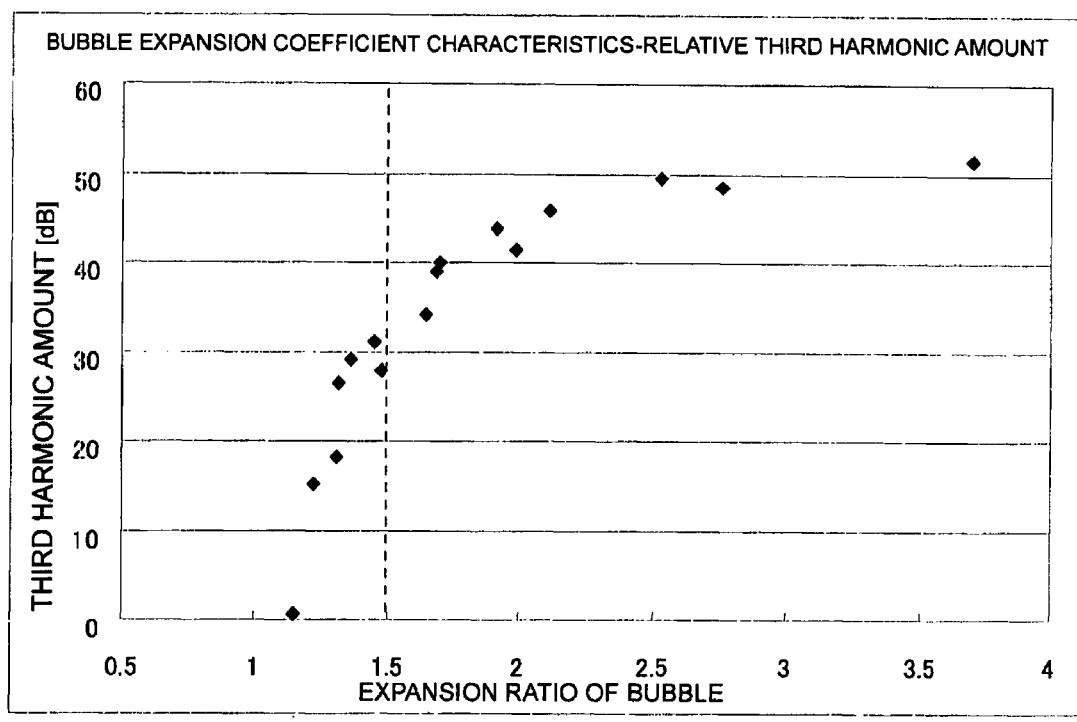
FIG. 5 is a view illustrating a correspondence relationship between an expansion ratio of bubbles and a signal amount of a harmonic component obtained from the bubbles.

FIG. 5 shows a correspondence relationship between the expansion ratio of the bubble and a signal amount of the harmonic component obtained from the bubble. More specifically, FIG. 5 plots the expansion ratio of the bubble in the horizontal axis and the third harmonic signal amount in the vertical axis observed when vibration was applied to a bubble having a radius of 1.25 µm with the ultrasound energy to be applied being fixed, under the conditions that the frequencies are 1.5, 2.5, 3.5, and 4.5 MHz, and the sound pressures are 100, 200, 300, and 400 kPa.

As can be seen from FIG. 5, in the range with a small expansion ratio of the bubble between 0.5 and 1.5, the signal amount of the third harmonic is relatively small and a variation of the signal amount relative to a variation of the expansion ratio is relatively large. On the other hand, in the range with a large expansion ratio of the bubble, which is 1.5 or higher, the signal amount of the third harmonic is relatively large and a variation of the signal amount relative to a variation of the expansion ratio is relatively small. As such, it can be expected that with expansion of a bubble by 1.5 fold or more, the third harmonic signal with high intensity can be obtained. Also, even with the expansion of the bubble by 2.5 fold or more, the increase in the harmonic signal amount remains substantially the same.

As described above, by expanding the bubble (microbubble) from about 1.5 fold to about 2.0 fold, a harmonic signal with an extremely high intensity can be generated from the bubble. It can also be understood that by applying ultrasound at a frequency which is lower than the resonance frequency of the bubble, it is possible to expand the bubble to a greater degree with an ultrasound signal at a lower sound pressure.

Conditions for detecting bubbles with high sensitivity will now be considered. As known as tissue harmonics, harmonic components are generated during propagation of ultrasound. The signal amount of the harmonics is substantially in proportion to a square of the sound pressure. Therefore, by transmitting ultrasound at a low frequency which is lower than the resonance frequency, it is possible to expand the bubble by 1.5 fold or more at a low sound pressure, so that the harmonic signal from the bubble can be increased while the harmonic single from a tissue can be reduced. Consequently, an extremely high CTR (Contrast to Tissue Ratio) can be achieved. Further, by expanding the bubble by 1.5 fold or more, the third or higher order harmonic components from the bubble are enhanced. As a higher order harmonic signal decreases to a greater degree during propagation in a tissue, by expanding the bubble by 1.5 fold or more and performing imaging using the third or higher order harmonic components, a higher CTR can be achieved.

Figure 6:
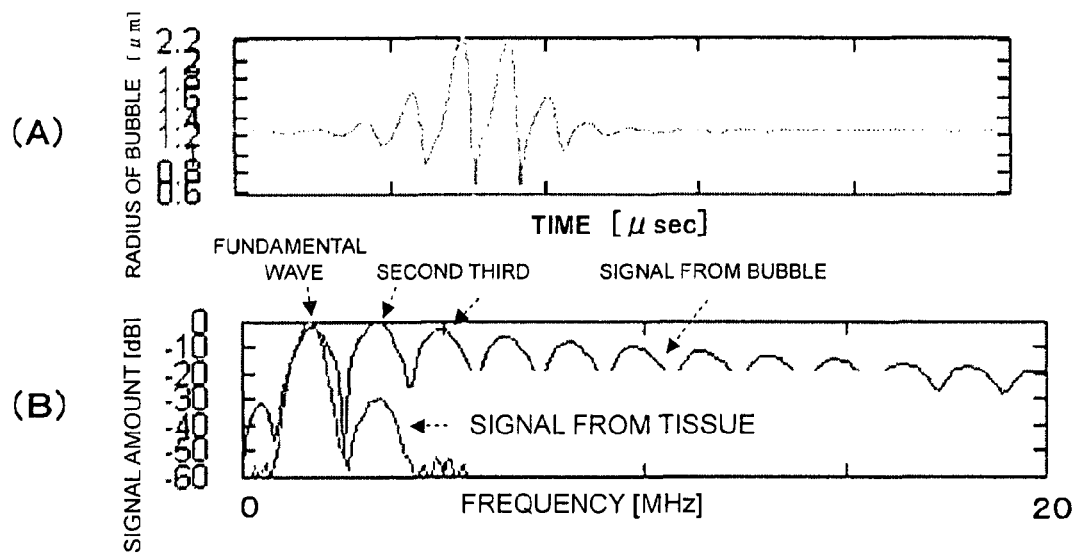
FIG. 6 is a view illustrating a simulation result of harmonics generated from tissue and harmonics obtained from bubbles.

FIG. 6 shows a result of simulation of harmonics generated from a tissue and harmonics from a bubble by using a convex abdomen probe. Numerical analysis using a KZK equation was performed with respect to non-linear propagation of ultrasound in a tissue. In this simulation, high-order harmonic signals were obtained during propagation of ultrasound in the tissue and from the bubble, under the conditions of the transmission frequency of 1.6 MHz and the sound pressure of 200 kPa within the tissue at a depth of 9 cm.

FIG. 6(A) indicates a vibration result of a bubble membrane at this time. The radius of the bubble expanded by about 1.75 fold, from 1.25 µm to 2.2 µm. FIG. 6(B) shows a comparison between a harmonic signal from the tissue and a harmonic signal from the bubble. The signal from the tissue was analyzed on the assumption that a signal generated during propagation of ultrasound was a signal reflected from a reflector within the tissue at the same position as the bubble. FIG. 6(B) shows a relative comparison of the signal amount between the harmonic signal from the tissue and the harmonic signal from the bubble, with the fundamental signals from the tissue and the bubble being 0 dB. The signal amounts of the harmonic signals from the bubble are substantially unchanged among the fundamental wave signal, the second harmonic signal, and the third fundamental signal. On the other hand, with regard to the signal amount of the harmonic signal from the tissue, the second harmonic decreases to −30 dB and the third harmonic decreases to −50 dB or less, relative to the fundamental signal.

Figure 7:
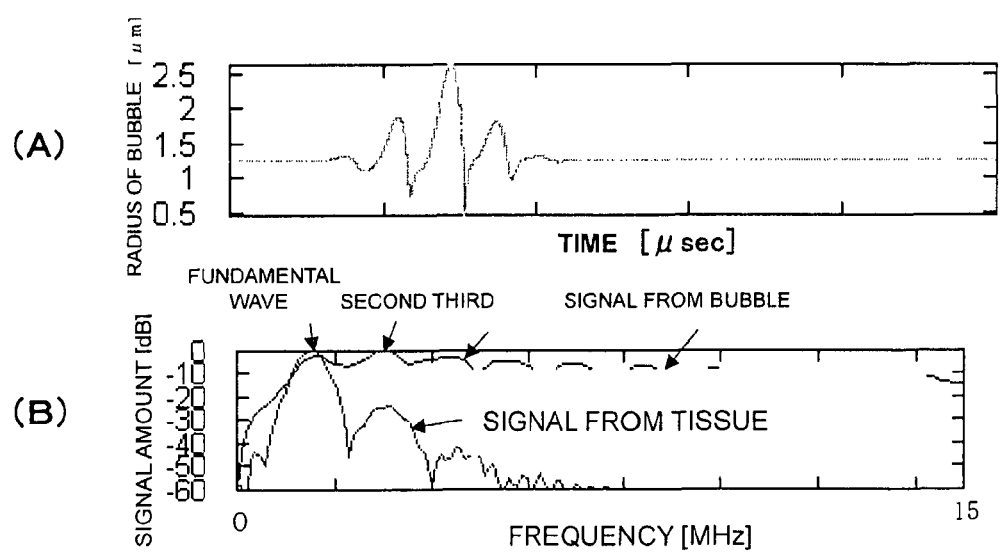
FIG. 7 is a view illustrating a simulation result of harmonics generated from tissue and harmonics obtained from bubbles.

FIG. 7 shows a result of simulation of harmonics generated from a tissue and harmonics from a bubble by using a linear probe. Numerical analysis using the KZK equation was performed with respect to non-linear propagation within a tissue. In this simulation, high order harmonic signals were obtained during propagation in the tissue and from the bubble, under the conditions of the transmission frequency of 1.5 MHz and the sound pressure of 200 kPa within the tissue at the depth of 9 cm.

FIG. 7(A) indicates a vibration result of a bubble membrane at this time. The radius of the bubble expanded about twofold from 1.25 µm to 2.5 µm. FIG. 6(B) shows a comparison between a harmonic signal of the tissue and a harmonic signal of the bubble. The signal from the tissue was analyzed on the assumption that a signal generated during propagation was a signal reflected from a reflector within the tissue at the same position as the bubble. FIG. 7(B) shows a relative comparison of the signal amount between the harmonic signal from the tissue and the harmonic signal from the bubble, with the fundamental signals from the tissue and the bubble being 0 dB. The signal amounts of the harmonic signals from the bubble are substantially the same among the fundamental wave signal, the second harmonic signal, and the third fundamental signal. On the other hand, with regard to the signal amount of the harmonic signal from the tissue, the second harmonic decreases to −30 dB and the third harmonic decreases to −50 dB or less, relative to the fundamental signal.

It can be understood from the above description that by excitation of bubbles at the low frequency which is the resonance frequency or lower, it is possible to expand the bubble by 1.5 fold or more even with low sound pressure transmission, so that a strong harmonic signal can be generated while the harmonic signal within the tissue can be suppressed. As a result, extremely high detection sensitivity and CTR can be achieved.

In ultrasound diagnostic apparatus, a probe with frequencies between 2.5 MHz and 12 MHz is normally used. In order to obtain high detection sensitivity with contrast echo, it is appropriate to use a probe with a low frequency, which allows transmission of ultrasound at a low frequency that is lower than the bubble resonance frequency. With the use of a probe having a center frequency of 3 MHz and a fractional bandwidth of 80%, it is possible to transmit ultrasound at the transmission frequency of 1.4 MHz and receive the third harmonic of 4.2 MHz. Here, while the transmission frequency of 1.4 MHz corresponds to a considerably lower region of the bandwidth of the probe, transmission is sufficiently possible because it is not necessary to generate high sound pressure. Further, although a third or higher-order harmonic signal can be generated from the bubble with a high intensity, the reception sensitivity cannot be obtained from the bandwidth of the probe in this case, and harmonic signals up to the third harmonics are used. However, it is obvious that the third or higher order harmonics may be used by employing a probe corresponding to the third or higher order harmonics.

Figure 8:
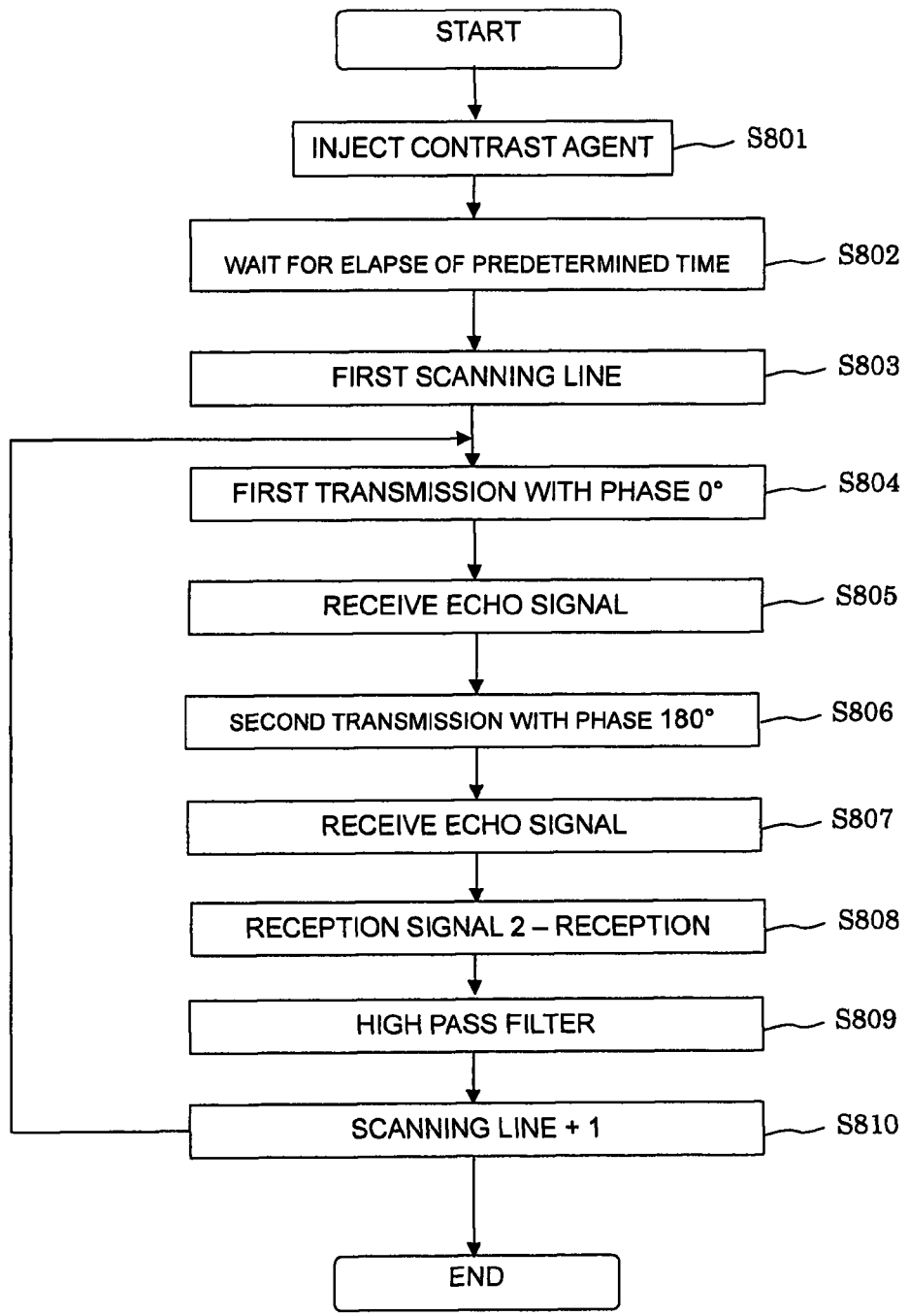
FIG. 8 is a flowchart for explaining image forming technology in which a third harmonic signal is utilized.

FIG. 8 is a flowchart for explaining image forming processing using a third harmonic signal by means of the ultrasound diagnostic apparatus illustrated in FIG. 1. First, a contrast agent is injected into a living organism (S801), and after elapse of an appropriate time until accumulation and capture of bubbles occurs within the living organism (S802), observation is started.

Once observation is started, the first scanning line (transmission beam direction) is selected (S803), a first low sound pressure pulse signal having a phase set to 0° is transmitted (S804), and a reception signal 1 which is an echo signal of the first pulse signal is received (S805). Further, on the first scanning line, a second pulse signal having a phase varied by 180° from that of the first transmission signal is transmitted (S806), and a reception signal 2 which is an echo signal thereof is received (S807). Here, at the time of transmission in steps S804 and S806, an ultrasound pulse having a center frequency of about 1.5 MHz and a transmission sound pressure of about 200 to 300 kPa, for example, is transmitted.

When only the third harmonic signal is used, by obtaining a difference between the two reception signals (S808), odd-number order signals are added with the identical phase, and even-number order signals are cancelled. Here, as the fifth or higher odd-number order harmonics, which are out of the bandwidth of the probe, are not contained in the reception signal, the first (the fundamental frequency) and the third signal components contained in the reception signal are extracted in the processing in step S808. Then, as the fundamental frequencies are also contained in the tissue signal in a large amount, the high pass filter is employed (S809) to extract only the third harmonic components. Then, by shifting the scanning line by one (S810) and repeating the processing from steps S804 to S809, a contrast image can be formed by the third harmonic obtained from a plurality of scanning lines.

By performing imaging using only the third harmonic signals, an image with a high CTR can be obtained because the third signal components from the tissue are extremely small. It should be noted that when an apparatus which uses only the third harmonic signal is configured, the addition processing unit 22 and the bandpass filter 26 illustrated in FIG. 1 may be omitted.

Here, the reception signal also contains a large amount of the second harmonic. Accordingly, by using the second harmonic and the third harmonic together, the signal intensity can be enhanced. This allows information from a deep portion where echo is weak to be imaged, and also allows expansion of the bandwidth of the signal amount, so that an image with a high resolution can be obtained.

Figure 9:
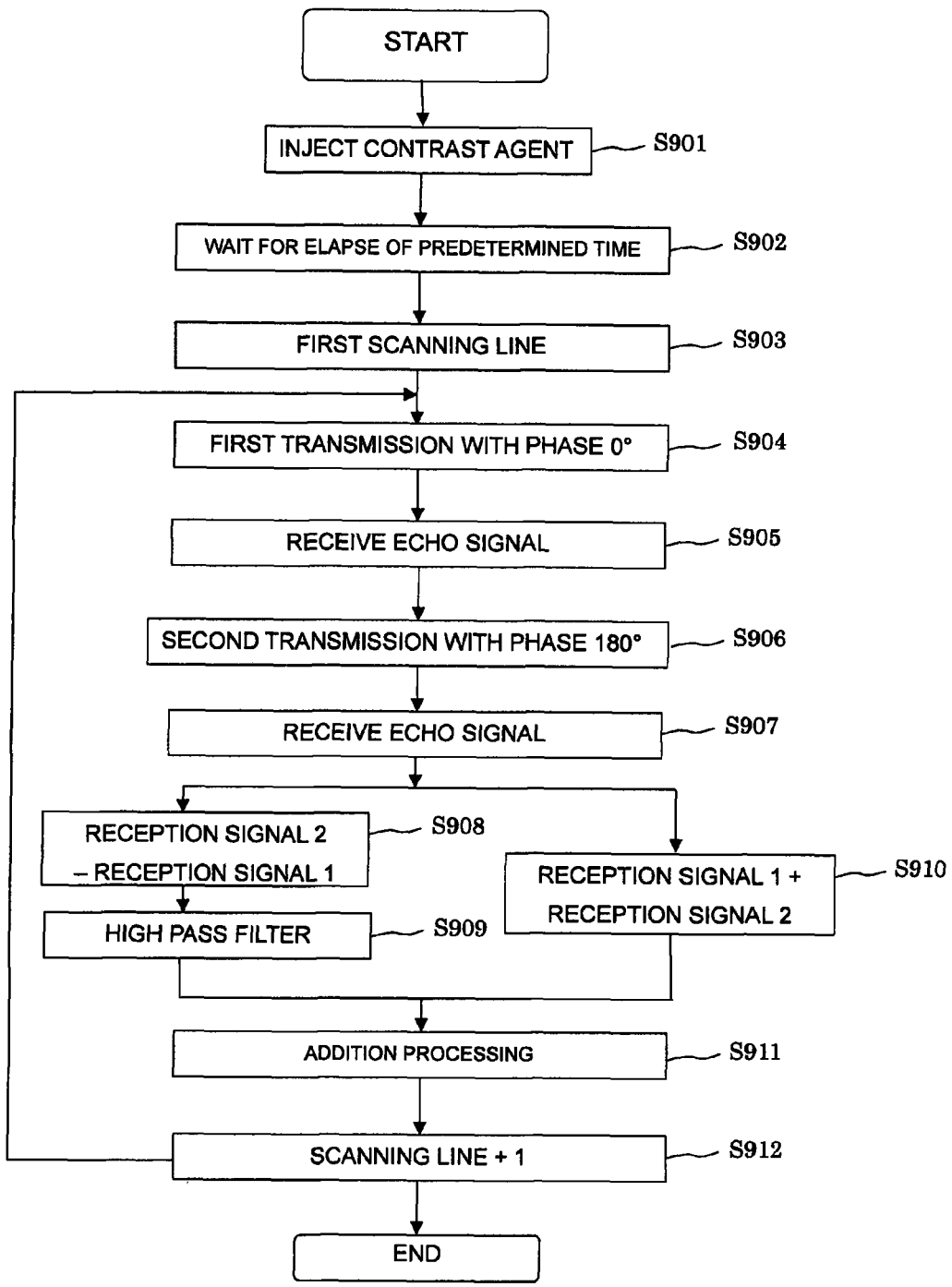
FIG. 9 is a flowchart for explaining an image forming technology in which second and third harmonic signals are utilized.

FIG. 9 is a flowchart for explaining image forming processing using second and third harmonic signals by means of the ultrasound diagnostic apparatus illustrated in FIG. 1. Here, the processing in steps S901 to S909 in FIG. 9 is the same as the processing in steps S801 to S809 in FIG. 8 and will therefore not be described.

In FIG. 9, in addition to the third harmonics, by adding the two reception signals (S910), even-number order signals contained in the reception signals are added with the identical phase and odd-number order signals are cancelled. Specifically, the fundamental wave and the third harmonic are removed and the second harmonic component is extracted. Then, by adding the second harmonic signal and the third harmonic signal (S911), a signal with a broad bandwidth and a high intensity can be obtained. Here, in FIG. 9, as in FIG. 8, by shifting the scanning line by one (S912) and repeating the processing from steps S904 to S911, a contrast image can be formed by the second and third harmonics obtained from a plurality of scanning lines.

When a large number of reflectors exist in higher density compared to the wavelength, and also at random, an echo and an interference pattern appear. This interference pattern is referred to as speckle, and becomes artifacts. When a large number of bubbles are present, speckle appears in the same manner. It is known that these interference patterns have different patterns depending on the frequencies, and frequency compounding is known as a method of reducing these interference patterns. Similarly, Akiyama et al. have proposed a method of adding high order harmonic images in order to reduce speckle noise appearing in a B-mode image (see "*Concerning Addition Method of High Order Harmonic Images for the purpose of Speckle Reduction*", by Yamanoto, Ozawa, and Akiyama, Technical Report of the Institute of Electronics, Information, and Communication Engineers, Vol. 102, No. 411 (20021018), PP. 19-24).

Figure 10:
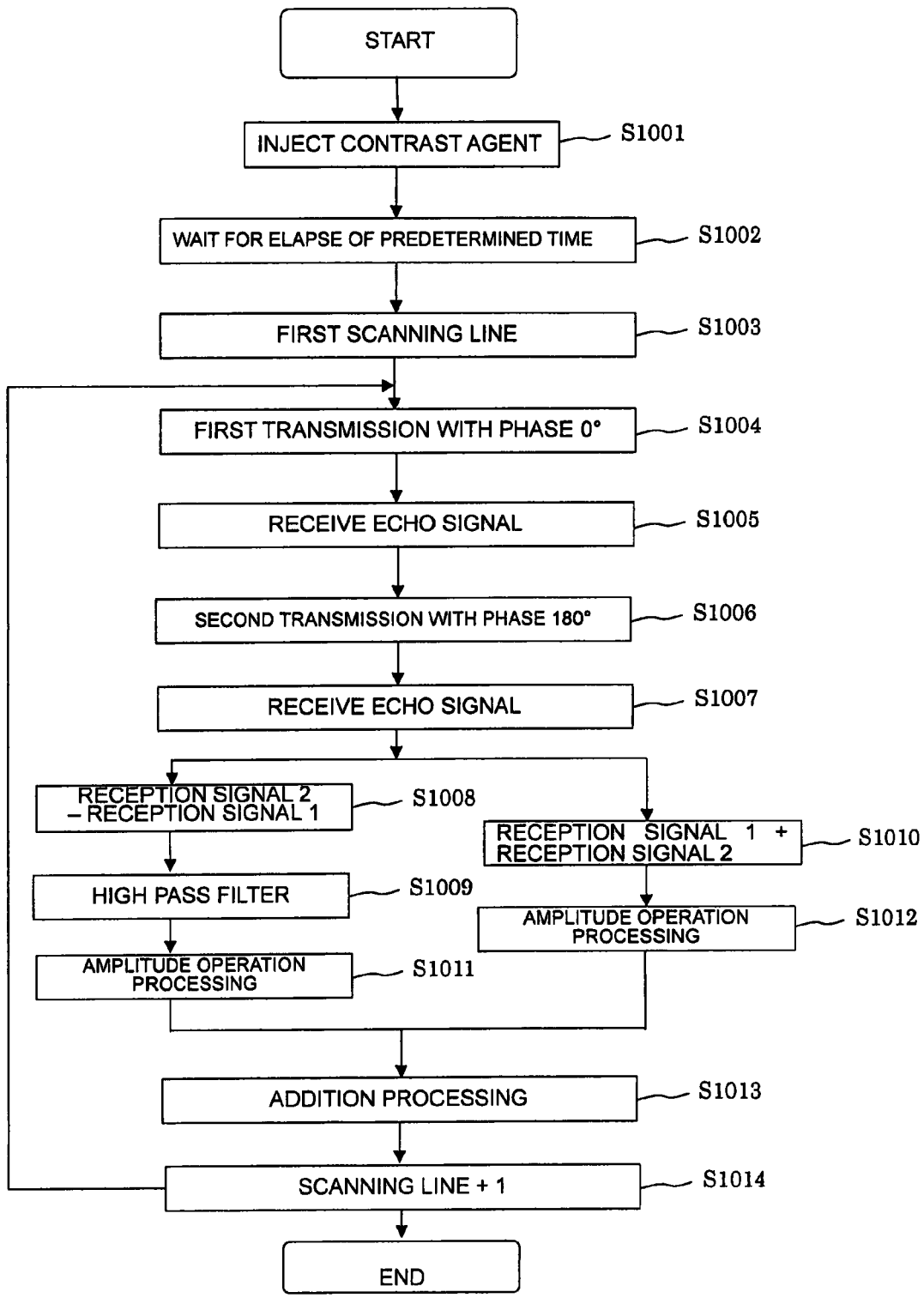
FIG. 10 is a flowchart for explaining processing for reducing speckles by incoherent superposition.

FIG. 10 is a flowchart for explaining the processing for reducing speckle by incoherent superposition. Specifically, FIG. 10 shows a processing flow for the purpose of speckle reduction of contrast echo by incoherent superposition using the second and third harmonics from the bubble. Here, the processing in steps S1001 to S1010 in FIG. 10 is the same as the processing in steps S901 to S910 in FIG. 9 and will therefore not be described.

In FIG. 10, amplitude operation processing (S1011) is performed with respect to the third harmonic component extracted by the processing in step S1009, and an envelope of the third harmonic component is consequently obtained. Similarly, amplitude operation processing (S1012) is performed with respect to the second harmonic component extracted by the processing in step S1010, and an envelope of the second harmonic component is consequently obtained. Then, the envelope of the third harmonic component and the envelope of the second harmonic component are added (S1013) to realize frequency compounding.

Here, in FIG. 10, as in FIGS. 8 and 9, by shifting the scanning line by one (S1014) and repeating the processing from steps S1004 to S1013, an ultrasound image can be formed.

Figure 11:
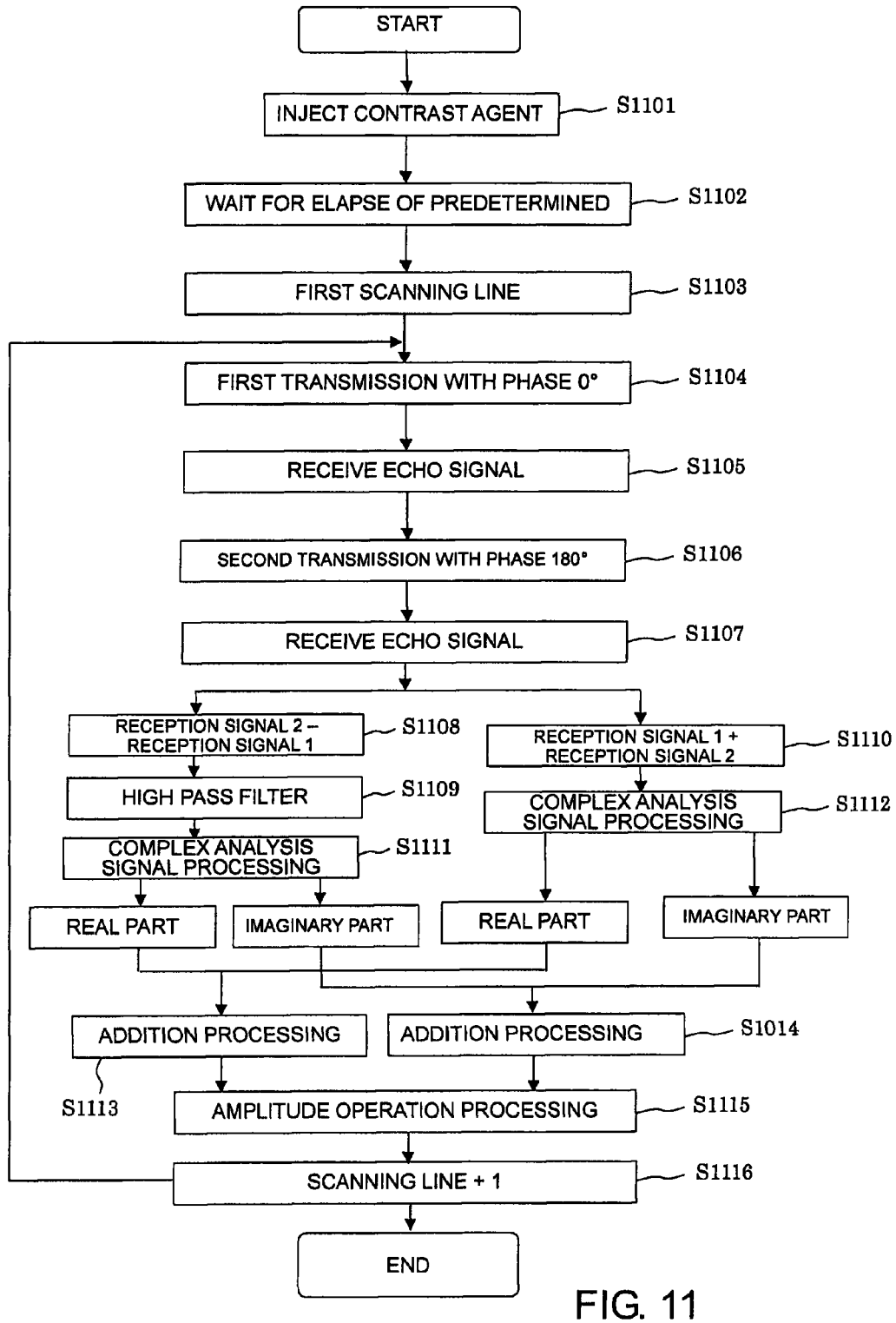
FIG. 11 is a flowchart for explaining processing for reducing speckles by coherent superposition.

FIG. 11 is a flowchart for explaining the processing for reducing speckle by coherent superposition. Specifically, FIG. 11 shows a processing flow for the purpose of speckle reduction of contrast echo by coherent superposition using the second and third harmonics from the bubble. Here, the processing in steps S1101 to S1110 in FIG. 11 is the same as the processing in steps S1001 to S1010 in FIG. 10 and will therefore not be described.

In FIG. 11, complex analysis signal processing (S1111) is performed with respect to the third harmonic component extracted by the processing in step S1109, and a real part and an imaginary part of the third harmonic component are consequently obtained. Similarly, complex analysis signal processing (S1112) is performed with respect to the second harmonic component extracted by the processing in step S1110, and a real part and an imaginary part of the second harmonic component are consequently obtained.

Then, the real part of the third harmonic component and the real part of the second harmonic component are added (S1113), and the imaginary part of the third harmonic component and the imaginary part of the second harmonic component are added (S1114). Further, amplitude operation processing (S1115) is performed based on the added real parts and the added imaginary parts, and consequently coherent superposition by the second harmonics and the third harmonics is realized. Here, in FIG. 11, as in FIG. 10, by shifting the scanning line by one (S1116) and repeating the processing from steps S1104 to S1115, an ultrasound image can be formed.

Next, another preferred embodiment of the present invention will be described.

Figure 12:
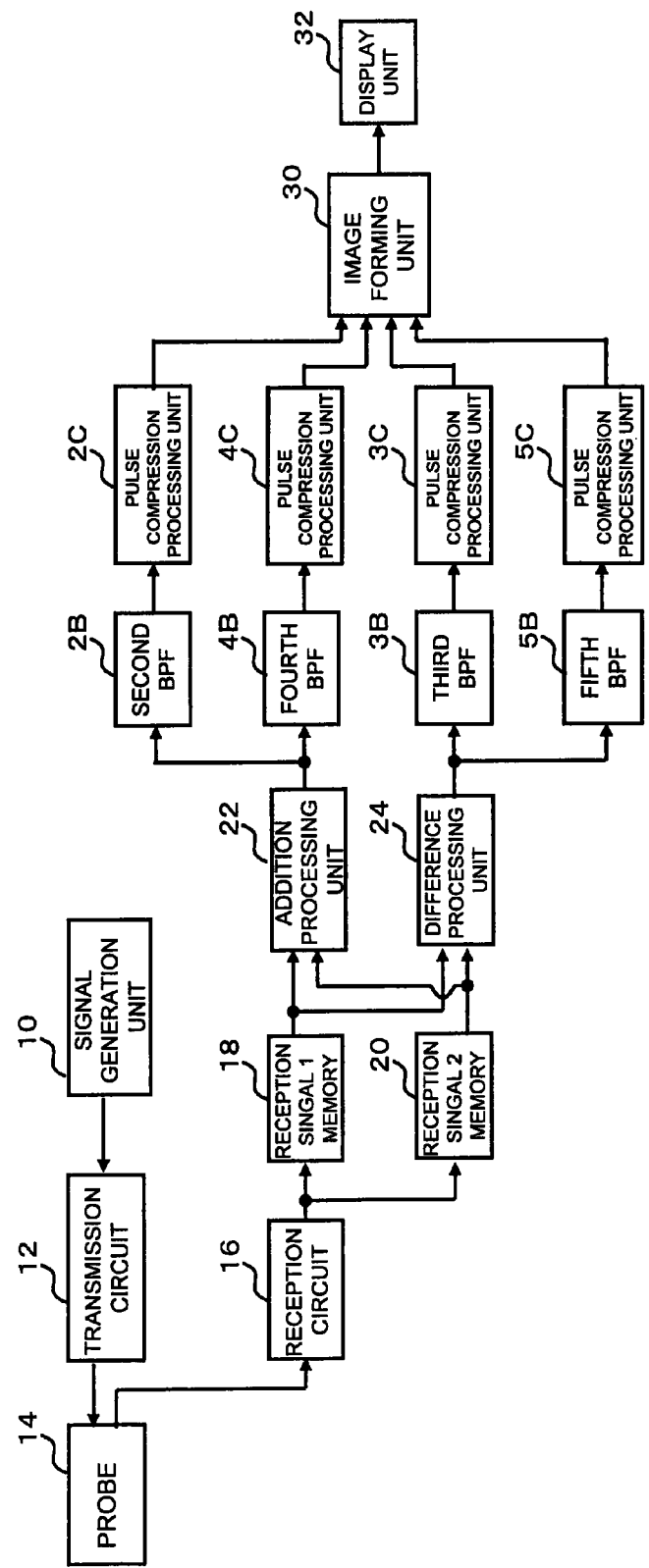
FIG. 12 is a block diagram illustrating another preferred embodiment of an ultrasound diagnostic apparatus according to the present invention.

FIG. 12 is a functional block diagram illustrating the overall structure of an ultrasound diagnostic apparatus according to another preferred embodiment of the present invention. The ultrasound diagnostic apparatus illustrated in FIG. 12 is suitable for forming an image by using a contrast agent including imaging bubbles (fine air bubbles such as microbubbles and nanobubbles). However, a subject to be diagnosed (i.e. a target subject) of the ultrasound diagnostic apparatus according to the present invention is not limited to microbubbles, and may be a tissue within a living organism, for example.

While, in the present embodiment, it is desirable to use a contrast agent suitable for imaging by ultrasound at low-middle sound pressure (e.g. "Sonazoid" (registered mark)), for example, the contrast agent used in the present invention is not limited to any specific contrast agent. The contrast agent is administered to a diagnostic site within a living organism, such as a blood vessel or a tumor, for example. After elapse of a predetermined time from administration of the contrast agent until the bubbles are accumulated or captured within the living organism, diagnosis is carried out by using the ultrasound diagnostic apparatus illustrated in FIG. 12.

A signal generation unit 10 is controlled by a control unit, which is not shown, to generate a transmission signal for transmitting ultrasound and output a transmission signal to a transmission circuit 12. In the present embodiment, as the transmission signal, a first chirp signal in which the frequency of a sine wave is continuously changed and a second chirp signal whose phase is inverted with respect to the phase of the first chirp signal (whose phase differs from that of the first chirp signal by 180°) are used.

Further, in the present embodiment, transmission control is performed such that ultrasound is transmitted at a transmission frequency bandwidth which is set using, as a reference, a resonance frequency of bubbles administered in the living organism and also at a transmission sound pressure which is set using, as a reference, an expansion ratio of the bubbles. For example, the signal generation unit 10 outputs a chirp signal having a waveform corresponding to the center frequency of approximately 1.5 MHz and the transmission sound pressure of approximately 200 to 300 kPa.

The transmission circuit 12 controls, based on the chirp signal output from the signal generation unit 10, a plurality of transducer elements provided in a probe 14 to form a transmission beam and then electronically scan the transmission beam thus formed, thereby forming a plurality of transmission beams over the entire region of the scanning region.

In the present embodiment, for each beam direction of the plurality of transmission beams, transmission and reception is performed twice. More specifically, after first transmission is performed based on the first chirp signal with regard to one beam direction and a first reception signal is obtained, second transmission follows, which is performed with regard to the same beam direction, based on the second chirp signal, and second reception signal is obtained. Then, after transmission and reception is performed twice with regard to one beam direction, the beam direction is changed and further transmission and reception is performed twice with regard to the new beam direction. In this manner, transmission and reception is executed twice for each beam direction over the entire region of the scanning region.

The probe 14 transmits and receives ultrasound with respect to a diagnostic region within a living organism to which a contrast agent is administered. The probe 14 includes a plurality of transducer elements for transmitting and receiving ultrasound, and the plurality of transducer elements are controlled by the transmission circuit 12 to scan the transmission beams. Further, the plurality of transducer elements receive ultrasound reflected by the living organism and output signals obtained from the reflected waves to a reception circuit 16. Here, transmission and reception of ultrasound may be performed by different transducer elements.

The reception circuit 16 applies phase alignment and summation processing to the signals obtained from the plurality of transducer elements of the probe 14 to form a reception signal corresponding to each of a plurality of transmission beams within the scanning region. As transmission is performed twice for each beam direction of the plurality of transmission beams in the present embodiment, the reception circuit 16 forms, for each beam direction, a first reception signal corresponding to the first chirp signal and a second reception signal corresponding to the second chirp signal. Then, for each beam direction, the first reception signal is stored in a reception signal 1 memory 18 and the second reception signal is stored in a reception signal 2 memory 20.

An addition processing unit 22, for each beam direction, reads the first reception signal and the second reception signal from the reception signal 1 memory 18 and the reception signal 2 memory 20, respectively, and then adds the first reception signal and the second reception signal. Because the first reception signal and the second reception signal are obtained from the chirp signals having phases inverted with respect to each other, according to the principle of phase inversion technology (or pulse inversion technology), an odd-number order signal is cancelled and only an even-number order signal remains as a result of the addition processing of the first reception signal and the second reception signal. More specifically, of the fundamental wave and the harmonic components contained in the reception signals, the fundamental wave and the odd-number order harmonic components are cancelled and the even-number order harmonic components are extracted.

A second bandpass filter (second BPF) 2B is a filter having a pass band corresponding to the second harmonics and extracts the second harmonic components from the even-number order harmonic components output from the addition processing unit 22. The second harmonic components thus extracted are subjected to pulse compression processing corresponding to the second harmonic components by a pulse compression processing unit 2C.

A fourth bandpass filter (fourth BPF) 4B is a filter having a pass band corresponding to the fourth harmonic and extracts the fourth harmonic components from the even-number order harmonic components output from the addition processing unit 22. The fourth harmonic components thus extracted are subjected to pulse compression processing corresponding to the fourth harmonic components by a pulse compression processing unit 4C.

A difference processing unit 24, for each beam direction, reads the first reception signal and the second reception signal from the reception signal 1 memory 18 and the reception signal 2 memory 20, respectively, and then computes a difference (performs subtraction processing) between the first reception signal and the second reception signal. According to the principle of phase inversion technology (or pulse inversion technology), an even-number order signal is cancelled and only an odd-number order signal remains as a result of the difference processing of the first reception signal and the second reception signal. More specifically, of the fundamental wave and the harmonic components, contained in the reception signals, the even-number order harmonic components are cancelled and the fundamental wave and the odd-number order harmonic components are extracted.

A third bandpass filter (third BPF) 3B is a filter having a pass band corresponding to the third harmonics and extracts the third harmonic components from the fundamental wave and the odd-number order harmonic components output from the difference processing unit 24. The third harmonic components thus extracted are subjected to pulse compression processing corresponding to the third harmonic components by a pulse compression processing unit 3C.

A fifth bandpass filter (fifth BPF) 5B is a filter having a pass band corresponding to the fifth harmonic and extracts the fifth harmonic components from the fundamental wave and the odd-number order harmonic components output from the difference processing unit 24. The fifth harmonic components thus extracted are subjected to pulse compression processing corresponding to the fifth harmonic components by a pulse compression processing unit 5C.

An image forming unit 30 forms image data of an ultrasound image based on the four harmonic components which are pulse-compressed second to fifth harmonic components obtained from the four pulse compression processing units (2C to 5C). The image forming unit 30, based on the four harmonic components, forms image data for each beam direction. Here, for formation of the image data, only one of the four harmonic components may be used or some or all of the four harmonic components are combined. Further, when the harmonic components are combined, weighting may be applied to each harmonic component.

The image forming unit 30, based on the image data formed with regard to the plurality of beam directions, forms image data of a two dimensional ultrasound image, for example. It is a matter of course that the ultrasound beam may be scanned in a three-dimensional manner to form image data of a three-dimensional ultrasound image. An ultrasound image corresponding to the image data formed in the image forming unit 30 is displayed on a display unit 32.

According to the present embodiment, as the transmission frequency is set using, as a reference, the resonance frequency of bubbles administered in the living organism and the transmission sound pressure is set using the expansion ratio of bubbles as a reference, it is possible, for example, to increase the harmonic components obtained from the bubbles while suppressing the harmonic components obtained from a real tissue, so that an ultrasound image with an extremely high CTR (Contrast to Tissue Ratio) can be obtained.

Figure 13:
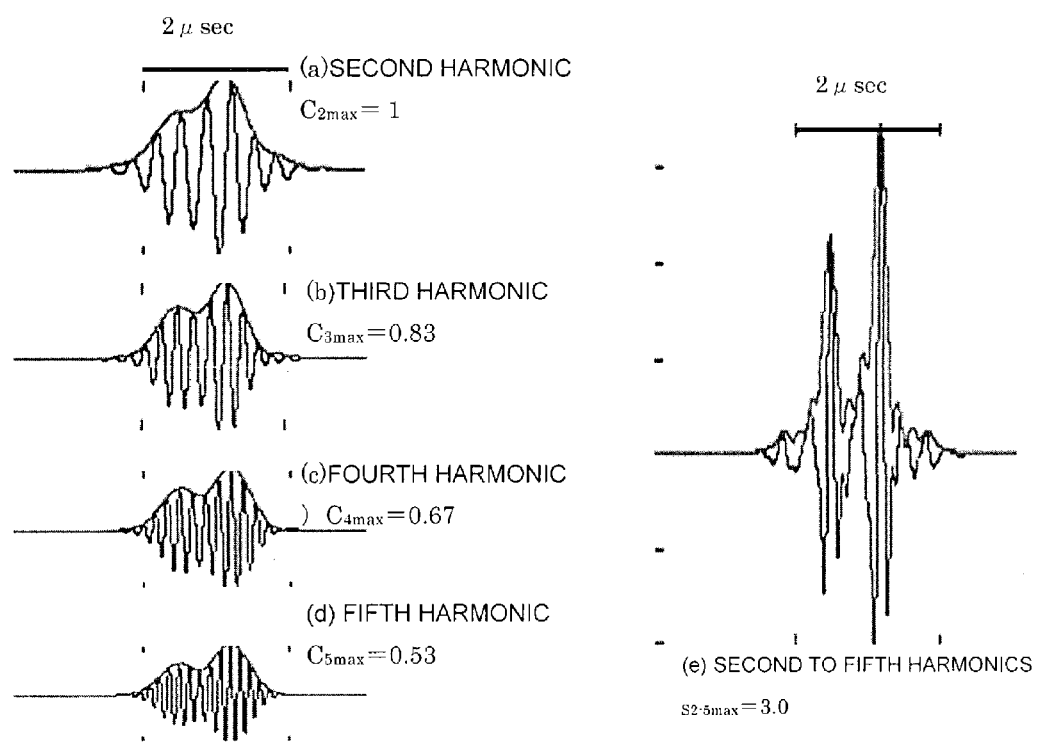
FIG. 13 is a view for explaining a signal waveform of each harmonic component contained in a reception signal from bubbles.

FIG. 13 is a view for explaining a signal waveform of each harmonic component contained in the reception signal from the bubble. Specifically, FIG. 13 shows signal waveforms (a) to (d) of the second, third, fourth and fifth harmonic components extracted separately from a signal obtained from a bubble under transmission conditions in FIG. 7, with the signal intensity of the second harmonic being specified as 1. FIG. 13 also shows a waveform (e) when the second to fifth harmonic components are added together.

As can be understood from FIG. 13, as a signal from the bubble including the fifth harmonic component can have an amplitude which is a half or more of the amplitude of the second harmonic component, it can be expected that use of the fifth harmonic is possible. Further, by adding the high-order harmonic from the second to fifth harmonics, the signal amplitude is tripled. Use of the third or higher order harmonics can be made possible by expanding the bubbles 1.5 fold or more with transmission of ultrasound at a low frequency. Further, when the higher order harmonics are added and used, the signal intensity can be increased and enhanced detection sensitivity can be expected.

As described above, by vibrating bubbles largely at a low frequency and also at a low sound pressure and using high order harmonics generated at that time, the Contrast to Tissue Ratio, CTR, can be drastically increased. In particular, when higher order harmonics, such as the fourth and fifth harmonics, are used, greater advantages can be obtained.

Considering imaging of a deep site, the frequency increases with the use of the high order harmonics, which results in increase in attenuation of a signal during propagation of ultrasound in a tissue and decrease in the signal intensity from the deep site. The attenuation of ultrasound during propagation in a tissue is generally said to be approximately 0.3 to 0.5 dB/(cm·MHz). Accordingly, the attenuation amount of the second harmonics and the fifth harmonics, when calculated as the intensity of signals which can be received at the time of transmission of ultrasound with the depth of 10 cm and 1.5 MHz for 0.4 dB/(cm·MHz), is −12 dB for the second harmonics and −30 dB for the fifth harmonics.

In FIG. 13, because the generated signal ratio between the second harmonics and the fifth harmonic from the bubbles is 1:0.53, the reception signal ratio including attenuation is 1:0.067. Similarly, the reception signal ratio between the second harmonic and the fourth harmonic is 1:0.17, and the reception signal ratio between the second harmonic and the third harmonic is 1:0.42. As the reception signal itself is smaller, due to effects of noise of the receiving amplifier or the like, Signal-to-Noise Ratio SNR reduces and high sensitivity cannot be obtained, even when high CTR is secured. As such, in order to obtain a contrast image with high sensitivity even at a deep site by utilizing high order harmonic signals which are characteristics of the bubble vibration, it is necessary to increase the signal amount.

In order to increase the signal amount from the bubbles, it is necessary to increase the transmission power to thereby increase the vibration amount of the bubbles. Accordingly, a case in which the transmission sound pressure is increased to thereby increase the vibration of the bubbles will be reviewed. As can be understood from the analysis results in FIG. 5, even if the transmission sound pressure is increased to cause the bubbles to vibrate to a great extent, the amount of generation of the third harmonic does not increase in a proportional manner. On the other hand, as the high order harmonics generated during propagation of ultrasound in a tissue is in proportion to a square of the sound pressure, an excessive increase in the sound pressure will not result in high detection sensitivity. There is also a concern that the bubbles collapse at the high sound pressure. Accordingly, in order to increase the signal amount, it is considered to be effective to increase the number of transmission pulses, rather than increasing the transmission sound pressure. However, when the number of transmission pulses is increased at a low frequency, the pulse length is extended to reduce the resolution in the depth direction.

FIG. 13 shows envelopes of the second to fifth harmonic signals, respectively. The shape of the envelope is determined by the envelope of transmission, and the resolution in the depth direction is not increased even in the high order harmonics. Here, it is desired that a reduction of the resolution in the depth direction associated with the use of a low frequency, particularly a reduction in the resolution caused by the use of a long pulse wave with regard to a deep subject, should be minimized. It is obviously desirable to increase the resolution.

One object of the present embodiment is to form an image with high resolution while maintaining the high detection sensitivity even in a deep site in the technology of generating a contrast image with high CTR, by receiving high order harmonics from bubbles by transmitting ultrasound at a low frequency and low sound pressure. In the present embodiment, basically, a long pulse is utilized to increase the signal amount, and for the purpose of securing the resolution in the depth direction, a chirp signal is transmitted, and a pulse compression filter is used to perform compression processing to obtain a short pulse.

While binary coding technology by means of a rectangular pulse is also used in the pulse compression technology, a rectangular signal, in which an odd-number order harmonic component is contained in a transmission signal itself, is not optimal to the present technology which utilizes the high order harmonics. One of the problems of the pulse compression technology in an actual ultrasound diagnostic apparatus is that a relatively long chirp signal cannot be utilized due to heat generation in the ultrasound probe. On the other hand, from analysis of bubble vibration, it is found that when bubbles are caused to vibrate at a low frequency, high order harmonics are generated at a low sound pressure. As a result, compared to when general transmission conditions are used, a longer chirp signal, that is a chirp signal with a larger signal amount, can be utilized. This is a result derived from the use of low frequency transmission and is one of the advantages obtained when combined with a chirp signal. Another characteristic obtained from the use of a chirp signal is that the higher the order of harmonics, the wider the frequency band and the sharper the pulse compression. Assuming that the start frequency and the stop frequency of a transmission chirp signal are $F_f$ and $F_l$, respectively, the frequency of each harmonic from the bubble is as follows:

TABLE 1

| | start frequency | stop frequency | frequency bandwidth |
|---|---|---|---|
| second harmonics: | $2F_f$ | $2F_l$ | $2(F_l\text{-}F_f)$ |
| third harmonics: | $3F_f$ | $3F_l$ | $3(F_l\text{-}F_f)$ |
| fourth harmonics: | $4F_f$ | $4F_l$ | $4(F_l\text{-}F_f)$ |
| fifth harmonics: | $5F_f$ | $5F_l$ | $5(F_l\text{-}F_f)$ |

In general, the pulse width and the band of a signal after pulse compression are in a relationship of $\tau=1/B$ (wherein $\tau$ is a pulse width and B is a bandwidth). Accordingly, with the use of the fifth harmonic, the pulse width can be compressed to one fifth, compared to the pulse compression of the fundamental wave, so that high resolution can be obtained.

Figure 14:
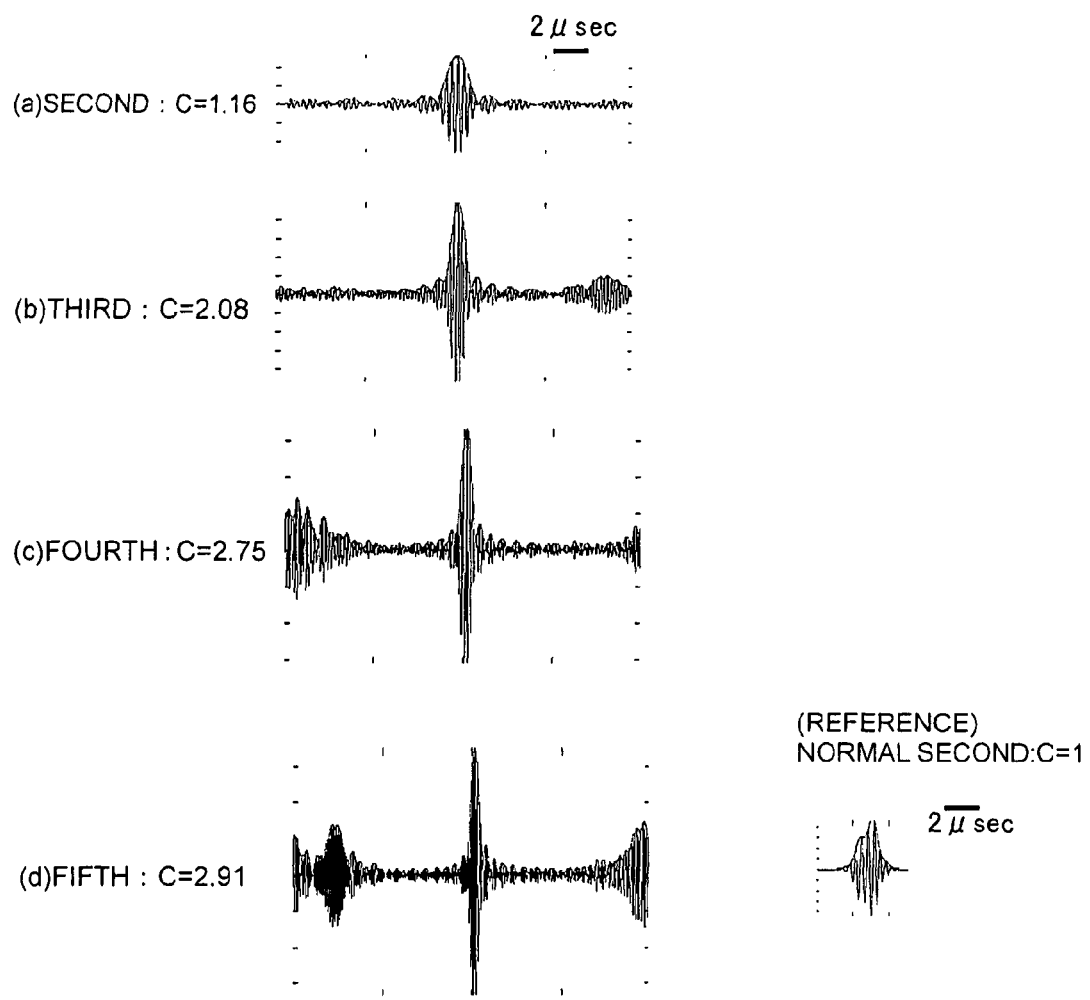
FIG. 14 is a view for explaining each harmonic component obtained when each harmonic component of a reception signal is pulse-compressed by using a chirp signal as a transmission signal.

FIG. 14 is a view for explaining each harmonic component of a reception signal which is pulse-compressed, when a chirp signal is used as a transmission signal. Specifically, FIG. 14 shows simulation results (a) to (d) concerning signals from a bubble obtained by pulse compression performed with respect to the second, third, fourth, and fifth harmonic signals, respectively, when a chirp signal with a sound pressure of 200 KPa, a start frequency of 1.19 MHz, a stop frequency of 1.69 MHz, a bandwidth of 500 KHz, and a pulse length of 15 μsec is transmitted. Further, the normal second harmonic indicated as (reference) in FIG. 14 is a second harmonic signal obtained from a bubble by using a normal transmission pulse (which is not a chirp signal) under the conditions of FIG. 13.

Regarding bubbles, calculation was performed using the conditions for a commercial available contrast agent, with the radius thereof assumed to be 1.25 μm. The peak value C of each waveform is indicated, with the peak value of the normal second harmonic being 1 for standardization. The peak value of the fifth harmonic after pulse compression increases to about three times as high as that of the normal second harmonic and also the pulse width thereof is approximately halved. Even in consideration of the frequency attenuation, at the depth of 10 cm, the signal intensity ratio between the normal second harmonic and the fifth harmonic is 1:0.36, and similarly the signal intensity ratio between the normal second harmonic and the fourth harmonic is 1:0.69. As such, the signal intensity which is approximately the same as that from the currently available bubbles can be expected. Also in a deep site, contrast ultrasound image with high CTR, that is, an image in which only bubbles are clearly imaged, can be obtained. In particular, in an intermediate or shallow portion of 5 cm or less, only bubbles can be imaged more clearly.

However, extremely high side lobes appear in the waveforms of the fourth and fifth harmonics after pulse compression, for the following reasons. Specifically, because, with the signal band of the third harmonic being between 3.57 MHz and 5.07 MHz, the signal band of the fourth harmonic being between 4.76 MHz and 6.76 MHz, the signal band of the fifth harmonic being between 5.95 MHz and 8.45 MHz, and the signal band of the sixth harmonics being between 7.14 MHz and 10.14 MHz, a third harmonic signal and a fifth harmonic signal superpose the fourth harmonic band, and similarly a fourth harmonic signal and a sixth harmonic signal superpose on the fifth harmonic band. Accordingly, signals which are not adaptable to the pulse compression procession are present.

To address this problem, in the present embodiment, as described above with reference to FIG. 12, after first transmission is performed based on the first chirp signal with regard to one beam direction and the first reception signal is obtained, second transmission follows and is performed with regard to the same beam direction based on the second chirp signal and the second reception signal is obtained. Then, the first reception signal and the second reception signal are added together, so that based on the principle of phase inversion phase, the fundamental wave and the odd-number order harmonic components are cancelled and the even-number order harmonic components are extracted. Further, a difference between the first reception signal and the second reception signal is calculated, and based on the principle of phase inversion technology, the even-number order harmonic components are cancelled and the fundamental wave and the odd-number order harmonic components are extracted. Thus, each harmonic component can be extracted while suppressing the mutual interference concerning the harmonic components of plural orders.

Figure 15:
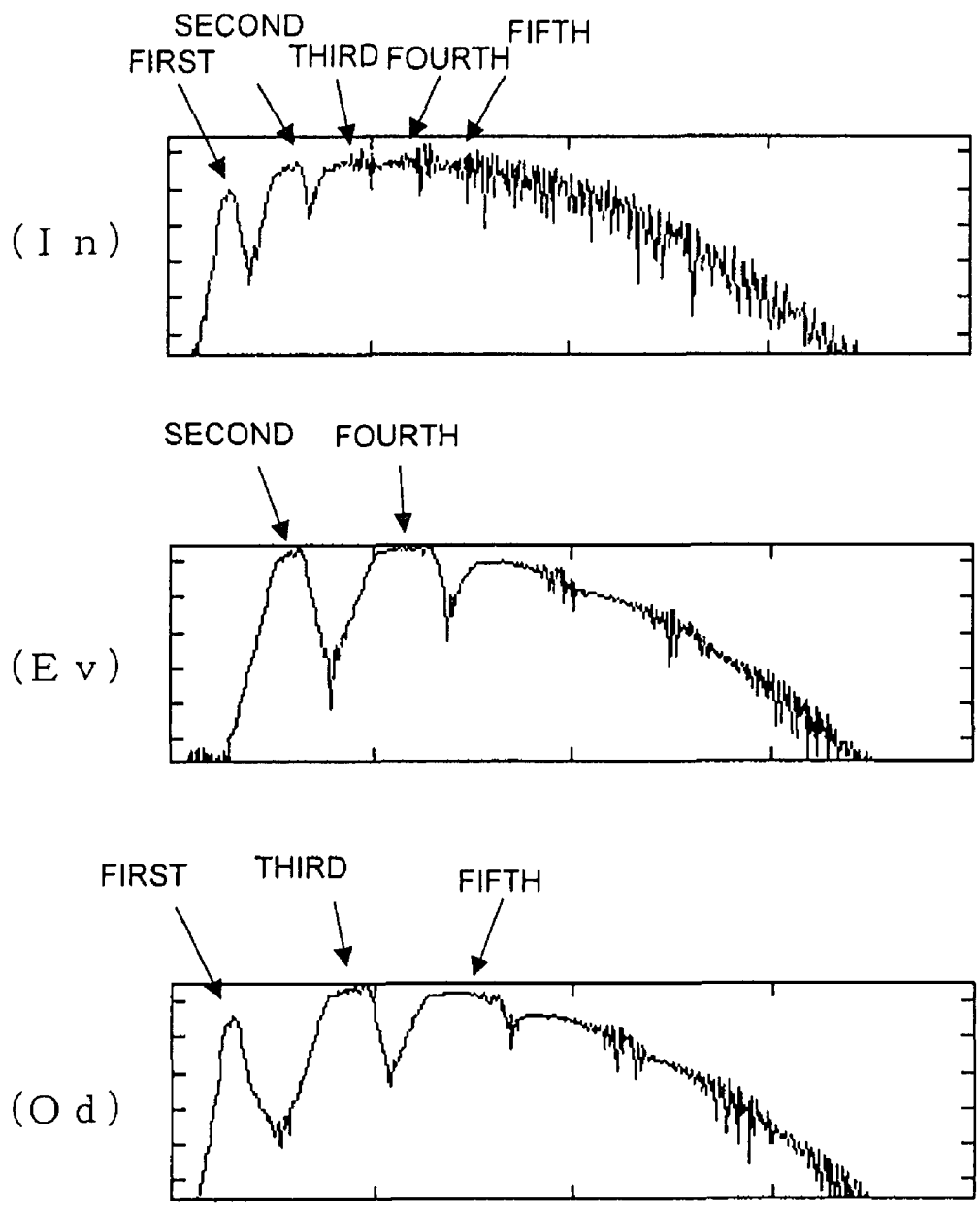
FIG. 15 is a view for explaining advantages achieved by addition processing and difference processing in the present embodiment.

FIG. 15 is a view for explaining effects of the addition processing and the difference processing according to the present embodiment. Specifically, FIG. 15 shows simulation results obtained when receiving a bubble signal by using a transducer having a center frequency of 7.2 MHz and a bandwidth of 70%, under the conditions that a chirp signal with a sound pressure of 200 KPa, a start frequency of 1.19 MHz, a stop frequency of 1.69 MHz, a bandwidth of 500 KHz, and a pulse length of 15 μsec is used. In FIG. 15(In), neither the addition processing nor the difference processing is performed and the reception signal contains harmonic components of integral number orders, from the first to fifth harmonic components.

FIG. 15(Ev) shows a simulation result obtained when a chirp signal having a positive phase and a chirp signal having a negative phase are transmitted, and two reception signals are added together. In FIG. 15(Ev), even-number order harmonic components, such as the second, the fourth, and so on, are extracted. On the other hand, FIG. 15(Od) shows a simulation result obtained when a chirp signal having a positive phase and a chirp signal having a negative phase are transmitted and subtraction is performed with regard to two reception signals. In FIG. 15(Od), odd-number order harmonic components, such as the first, the third, the fifth, and so on, are extracted.

Figure 16:
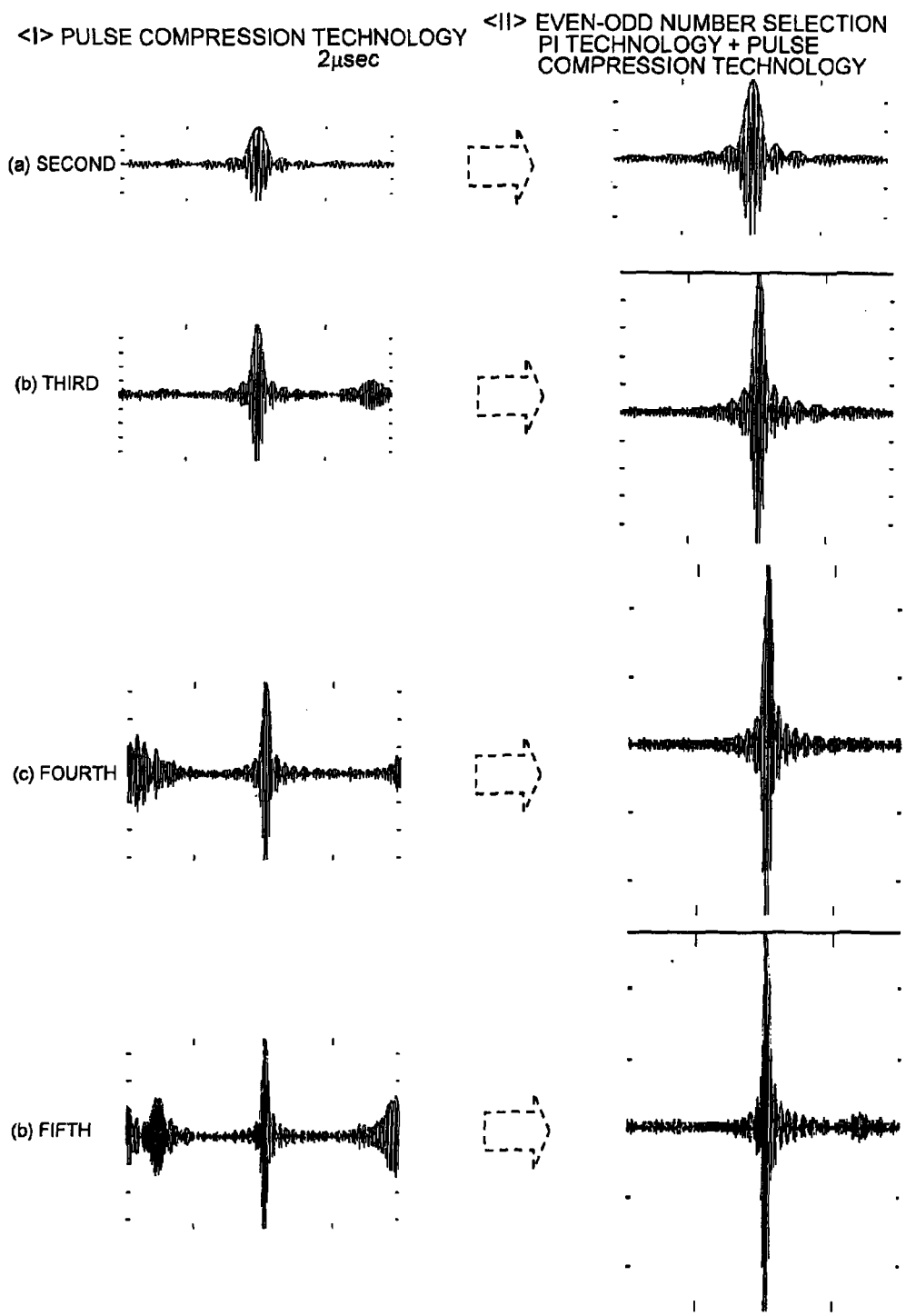
FIG. 16 is a view for explaining each harmonic component obtained when PI technology and pulse compression technology are combined.

FIG. 16 is a view for explaining each harmonic component obtained when the phase inversion (PI) technology and the pulse compression technology are combined. In FIG. 16, independent transducers for transmitting and receiving, respectively, which are a transmitting transducer having a center frequency of 1.44 MHz and a fractional bandwidth of 50% and a receiving transducer having a center frequency of 7.2 MHz and a fractional bandwidth of 70%, are assumed, and a simulation result of a bubble signal obtained under the same conditions as those in FIG. 14, in which a chirp signal with a sound pressure of 200 KPa, a start frequency of 1.19 MHz, a stop frequency of 1.69 MHz, a bandwidth of 500 KHz, and a pulse length of 15 μsec is used, is illustrated. Here, FIG. 16<I> illustrates, for reference, the second harmonic signal (a), the third harmonic signal (b), the fourth harmonic signal (c), and the fifth harmonic signal (d) obtained when only the pulse compression is used.

In the present embodiment, with the use of the principle of phase inversion technology (pulse inversion technology), odd-number harmonics and even-number harmonics are separated from each other and thereafter the pulse compression processing is performed in accordance with each high order harmonic. FIG. 16<II> (a) to (d) illustrates the resulting second, third, fourth, and fifth harmonics after the pulse compression processing which are obtained in this manner. In the present embodiment, as illustrated in FIG. 16<II>, as can be understood from comparison with the example of FIG. 16<I>, side lobes are drastically reduced in the pulse compression processing of the third, fourth, and fifth harmonics.

A signal contained after the addition pulse inversion will be considered. In this case, only the even-number order harmonic components, such as the second, fourth, and sixth harmonic components, are extracted. Accordingly, the signal bandwidth of the second harmonics is between 2.38 MHz and 3.38 MHz, the signal bandwidth of the fourth harmonics is between 4.76 MHz and 6.76 MHz, and the signal bandwidth of the sixth harmonics is between 7.14 MHz and 10.14 MHz, and the band of the fourth harmonics does not contain other harmonic signals. As a result, the pulse compression processing is performed appropriately. Similarly, with regard to the pulse compression processing concerning the fifth harmonics, an overlapping relationship between the third harmonic components and the fifth harmonic components, and between the fifth harmonic components and the seventh harmonic components, should be considered. Here, while a region in which the bandwidth of the fifth harmonics and the bandwidth of the seventh harmonic slightly overlap each other is present, the side lobes can be drastically suppressed.

By causing bubbles to oscillate under predetermined conditions, high order harmonics are generated with a high efficiency. With the use of a chirp signal as a transmission signal, the higher the order of high order harmonics, the wider the signal bandwidth. The compression ratio is increased as the bandwidth of a signal becomes wider, even when the signal amount remains unchanged, resulting in a higher peak of the signal. As such, with the use of a chirp signal, high order harmonics from the bubble can be extracted in the form of a signal having a high peak value. Then, in combination of this technology with technology of extracting odd-number harmonics and even-number harmonics separately, the bandwidth of each high-order harmonic signal can be widened maximally, and also overlapping between the bandwidths can be reduced, thereby suppressing side lobes.

In the present embodiment, in consideration of the depth of a subject to be observed, the detection sensitivity, the resolution, and so on, the frequency and the bandwidth of a transmission chirp signal and restriction to the order of high order harmonics are determined. In this case, preferable conditions would be to set the frequency and the bandwidth of the transmission chirp signal such that the maximum frequency of the frequency band of high order harmonics to be used is the same as the minimum frequency of the frequency band contained in two higher order harmonics. This setting allows an image having a narrow pulse width, small side lobes, and an excellent resolution in the depth direction to be realized.

Further, in the pulse inversion technology, due to transmission being performed twice, the signal intensity is doubled. On the other hand, regarding electric noise of the reception amplifier or the like which is concerned with regard to a signal from a deep site, because, due to addition being performed twice, the amplitude of the signal becomes √ double (the square root of a double), the signal to noise ratio SNR is increased by √ double (the square root of a double: 3 dB).

Figure 17:
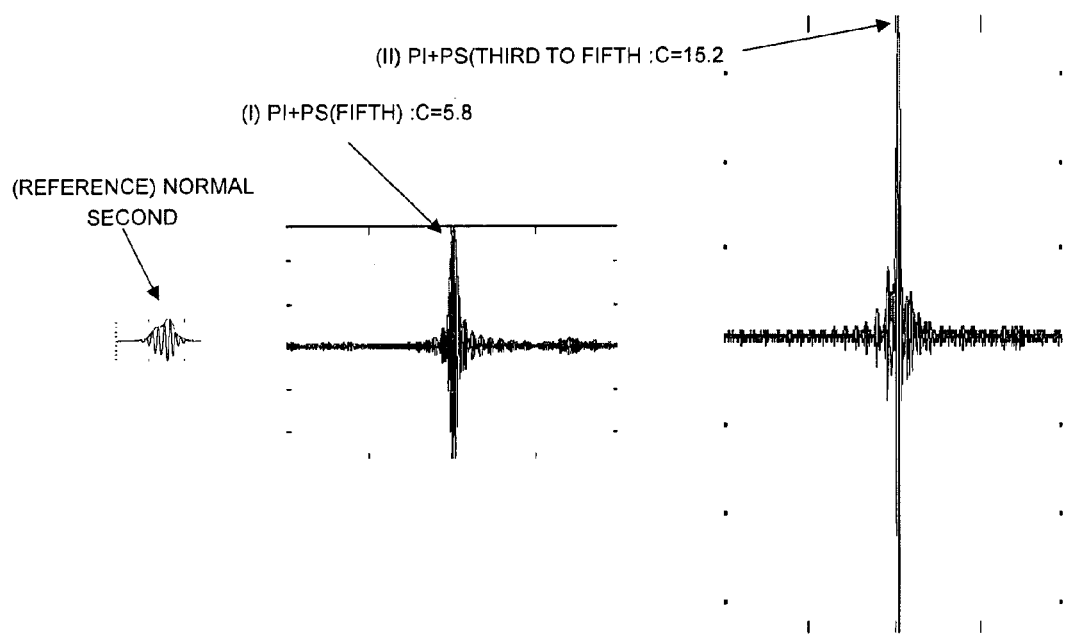
FIG. 17 is a view for explaining a combination of harmonic components of multiple orders.

FIG. 17 is a view for explaining a combination of harmonic components of multiple orders. In FIG. 17, effects obtained when, with the use of the principle of phase inversion technology (pulse inversion technology), after odd-number order harmonics and even-number order harmonics are separated from each other, the pulse compression processing is performed in accordance with each high order harmonic, and the third, fourth, and fifth harmonic signals are added. With addition of three harmonic signals as illustrated in FIG. 17(II), the signal intensity is amplified 15.2 times as much as with the use of a conventional simple pulse method illustrated as (reference) and 2.6 times as much as that of only the fifth harmonics illustrated in FIG. 17(I). Further, with addition of three harmonic signals, the frequency band of pulse compression is widened to 6 MHz, the pulse width is about 0.17 μsec, and the resolution in the depth direction is increased to 0.3 mm.

FIG. 18 is a chart illustrating a comparison result between the present embodiment and the normal PI technology. In the present embodiment, pulse compression technology in which a chirp signal is used and PI technology are combined to extract each harmonic component, whereas in normal PI technology, a chirp signal is not used. FIG. 18 shows comparison results concerning the bubble signal peak value C, the tissue signal peak value T, the Contrast to Tissue Ratio CTR, and the pulse width. For example, by combining the fourth and fifth harmonics, in the present embodiment, the signal value is increased 3.51 fold (11 dB), the CTR is increased 140 fold (42.9 dB), and the pulse width is increased to 0.22 μsec.

Figure 19:
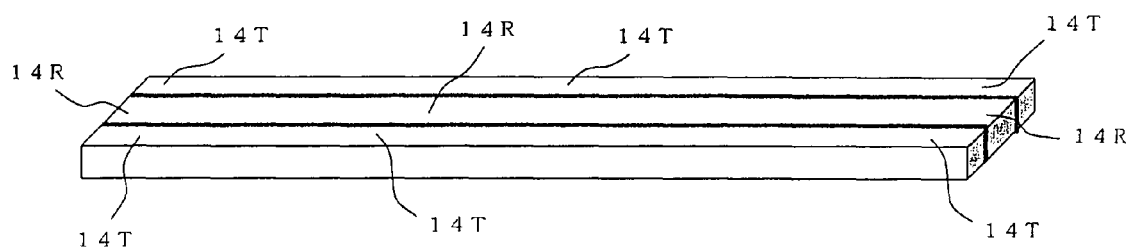
FIG. 19 is a view illustrating a transducer which is preferable for the present embodiment.

FIG. 19 is a diagram for explaining a transducer preferable for the present embodiment. FIG. 19 illustrates an example transducer having the probe 14 (see FIG. 12). The transducer is composed of a transmitting transducer 14T and a receiving transducer 14R.

The receiving transducer 14R provided on the inner side is formed of 128 channels of receiving high frequency transducer elements. Each of the high frequency transducer elements corresponds to the frequency band of the harmonic component of a reception signal, and the center frequency thereof is preferably about 7.2 MHz. Further, two lines of transmitting transducers 14T are provided on both outer sides so as to sandwich the receiving transducer 14R. Each line of the transmitting transducer 14T is composed of 64 channels of transmitting transducer elements. Each of the transmitting transducer elements corresponds to the frequency band of the transmission signal (the first chirp signal and the second chirp signal), and the center frequency thereof is preferably about 1.4 MHz.

Figure 20:
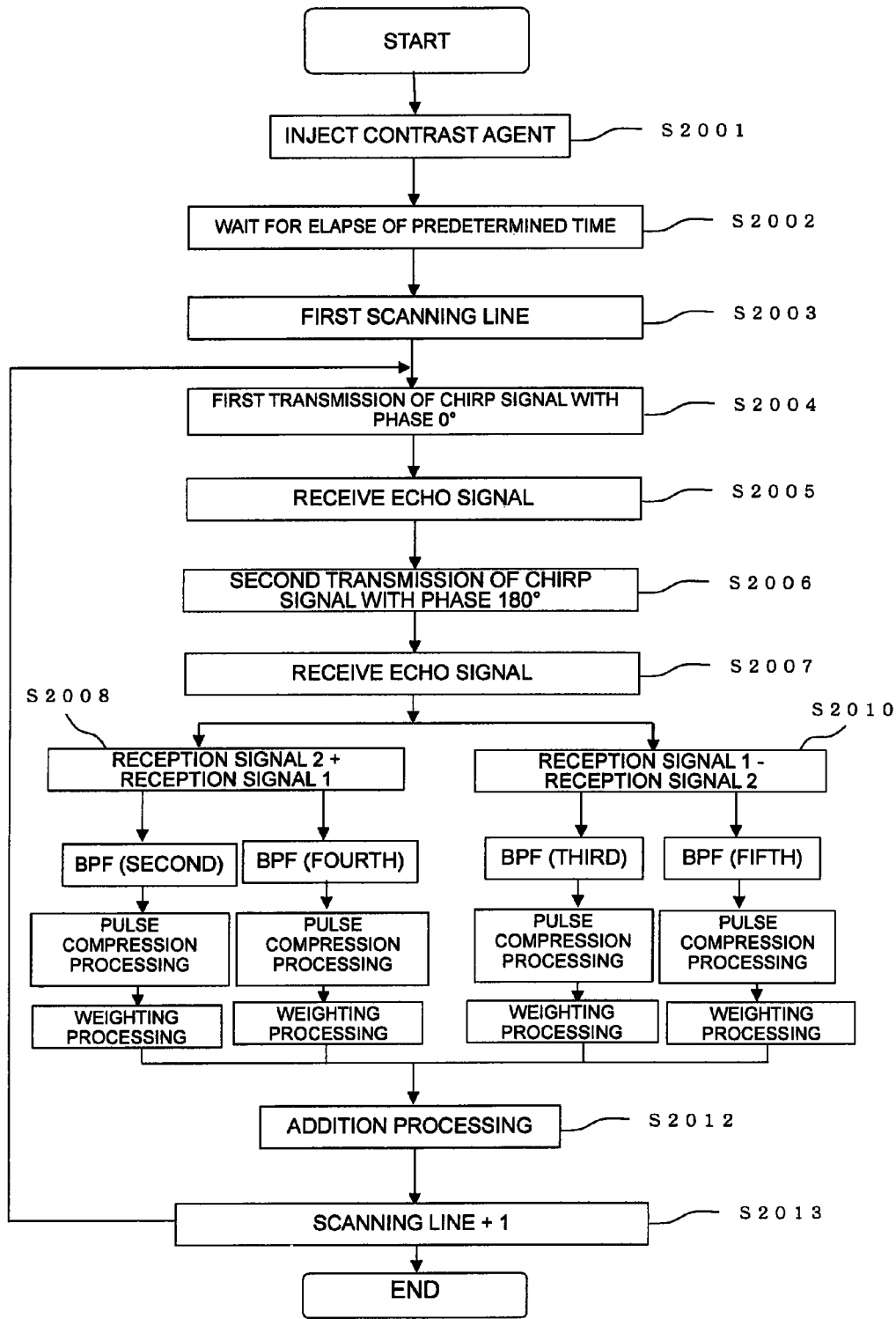
FIG. 20 is a view for explaining an image forming processing method according to the present embodiment.

FIG. 20 is a view for explaining an image forming processing method according to the present embodiment, and is a flowchart of image forming processing by the ultrasound diagnostic apparatus shown in FIG. 12. The processing of each step of the flowchart in FIG. 20 will be described below.

First, a contrast agent is injected into a living organism (S2001), and after elapse of an appropriate time until accumulation and capture of bubbles occurs within the living organism (S2002), observation is started. Once observation is started, the first scanning line (transmission beam direction) is selected (S2003), a first time chirp signal having a phase set to 0° (a first chirp signal) is transmitted (S2004), and a first reception signal which is an echo signal of the first chirp signal is received (S2005). Further, on the first scanning line, a second time chirp signal (a second chirp signal) having a phase varied by 180° from that of the first transmission signal is transmitted (S2006), and a second reception signal which is an echo signal thereof is received (S2007).

Once the first reception signal and the second reception signal are obtained, addition processing is performed with respect to these signals (S2008). Because the first reception signal and the second reception signal are obtained from the chirp signals having their phases inverted with respect to each other, due to the principle of phase inversion technology, as a result of the addition processing of the first reception signal and the second reception signal, odd-number order signals are cancelled and only even-number order signals remain. In the present embodiment, the second and fourth harmonic components, for example, are extracted as the even-number order signals.

More specifically, after the addition processing performed in S2008, the second harmonic components are extracted by the second BPF (indicated by numeral reference 2B in FIG. 12), and then pulse compression processing is performed with respect to the second harmonic components. Further, after the addition processing performed in S2008, the fourth harmonic components are extracted by the fourth BPF (indicated by numeral reference 4B in FIG. 12), and then pulse compression processing is performed with respect to the fourth harmonic components.

Also, after the step S2007 where the first reception signal and the second reception signal are obtained, the difference processing is performed with respect to these signals (S2010). Due to the principle of phase inversion technology, as a result of the difference processing of the first reception signal and the second reception signal, even-number order signals are cancelled and only odd-number order signals remain. In the present embodiment, the third and fifth harmonic components, for example, are extracted as the odd-number order signals.

More specifically, after the difference processing performed in S2010, the third harmonic components are extracted by the third BPF (indicated by numeral reference 3B in FIG. 12), and then pulse compression processing is performed with respect to the third harmonic components. Further, after the difference processing performed in S2010, the fifth harmonic components are extracted by the fifth BPF (indicated by numeral reference 5B in FIG. 12), and then pulse compression processing is performed with respect to the fifth harmonic components.

Here, weighting processing is performed as required, with respect to each harmonic component which has been pulse compressed. For example, the harmonic components are added with weighting in accordance with the characteristics of an image to be formed. In order to obtain an image with a high Tissue to Contrast Ratio (CTR), weighting is set such that only the fifth harmonic components are added. Alternately, weighting may be performed such that all the harmonic components are added, if high resolution in the depth direction is required. It is also possible to vary a ratio of weighting in accordance with the depth.

When four harmonic components from the second to fifth harmonic components which are pulse compressed are obtained as described above, addition processing is performed with respect to these four harmonic components (S2012). Here, this addition processing may be executed after weighting processing is performed with respect to each harmonic component, as necessary. Consequently, based on the four harmonic components from the second harmonic component to the fifth harmonic component having been pulse compressed, image data of an ultrasound image on the first scanning line is formed. Then, by shifting the scanning line by one line (S2013) and repeating the processing from step S2004 to step S2012, image data is formed on a plurality of scanning lines, so that a contrast image, for example, can be formed.

While the preferred embodiments of the present invention have been described using specific terms, such description is for illustrative purposes only in terms of all respects, and it is to be understood that changes and variations may be made without departing from the spirit or scope of the appended claims.

What is claimed is:

1. An ultrasound diagnostic apparatus, comprising:
a probe that transmits and receives ultrasound with respect to a diagnostic region including a bubble;
a transmission control unit that controls the probe to transmit ultrasound under transmission conditions which are set based on structural characteristics of a bubble;
a reception processing unit that obtains a reception signal corresponding to ultrasound received by the probe;
a harmonic extraction unit that processes the reception signal to extract a harmonic component contained in the reception signal; and
an image forming unit that forms image data concerning the bubble based on the harmonic component,
wherein the transmission control unit controls the probe to transmit the ultrasound at a transmission frequency which is set using a resonance frequency of the bubble as a reference and at a transmission sound pressure which is set using an expansion ratio of the bubble as a reference,
wherein the control unit is configured to determine the transmission frequency and the sound pressure based on harmonic signals of the bubble being substantially the same as fundamental signals of the bubble while harmonic signals from the tissue being substantially lower relative to fundamental signals from the tissue.

2. The ultrasound diagnostic apparatus according to claim 1, wherein
the transmission frequency is set equal to or lower than the resonance frequency of the bubble.

3. The ultrasound diagnostic apparatus according to claim 1, wherein
the transmission control unit, based on a correspondence between the expansion ratio of the bubble and a signal amount of the harmonic component which can be obtained from the bubble, sets the transmission sound pressure such that of two ranges that are a range with a small expansion ratio, in which the signal amount is relatively small and a variation of the signal amount with respect to a variation of the expansion ratio is relatively large, and a range with a large expansion ratio, in which the signal amount is relatively large and a variation of the signal amount with respect to a variation of the expansion ratio is relatively small, the expansion ratio falls within the range with a large expansion ratio.

4. The ultrasound diagnostic apparatus according to claim 1, wherein
the transmission frequency is set equal to or lower than the resonance frequency of the bubble, and the transmission sound pressure is set such that the expansion ratio of the bubble is 1.5 or higher.

5. The ultrasound diagnostic apparatus according to claim 1, wherein
the transmission control unit controls the probe to transmit ultrasound corresponding to each of a first transmission signal and a second transmission signal, phases of the first transmission signal and the second transmission signal being inverted with respect with each other, and
the harmonic extraction unit extracts the harmonic component based on a first reception signal corresponding to the first transmission signal and a second reception signal corresponding to the second transmission signal.

6. The ultrasound diagnostic apparatus according to claim 5, wherein
the harmonic extraction unit extracts the harmonic component based on at least one of addition processing and subtraction processing performed between the first reception signal and the second reception signal.

7. The ultrasound diagnostic apparatus according to claim 6, wherein
the harmonic extraction unit extracts an even-number order harmonic component by the addition processing performed between the first reception signal and the second reception signal.

8. The ultrasound diagnostic apparatus according to claim 6, wherein
the harmonic extraction unit extracts an odd-number order harmonic component by the subtraction processing performed between the first reception signal and the second reception signal.

9. The ultrasound diagnostic apparatus according to claim 6, wherein
the harmonic extraction unit extracts a second harmonic component and a fourth harmonic component by the addition processing performed between the first reception signal and the second reception signal, and extracts a third harmonic component and a fifth harmonic component by the subtraction processing performed between the first reception signal and the second reception signal.

10. The ultrasound diagnostic apparatus according to claim 1, wherein
the transmission control unit controls the probe to transmit ultrasound corresponding to each of a first chirp signal and a second chirp signal, phases of the first chirp signal and the second chirp signal being inverted with respect with each other,
the reception processing unit obtains a first reception signal corresponding to the first chirp signal and a second reception signal corresponding to the second chirp signal, and
the harmonic extraction unit extracts the harmonic component based on at least one of addition processing and subtraction processing performed between the first reception signal and the second reception signal,
the ultrasound diagnostic apparatus further comprising:
a pulse compression processing unit that applies pulse compression processing to the harmonic component which is extracted.

11. The ultrasound diagnostic apparatus according to claim 10, wherein
the harmonic extraction unit extracts the harmonic components of a plurality of orders by the addition processing and the subtraction processing, and
the pulse compression processing unit applies the pulse compression processing to each order harmonic component.

12. The ultrasound diagnostic apparatus according to claim 11, wherein the image forming unit forms image data of an ultrasound image including the bubble, based on a composite signal obtained by combining harmonic components of a plurality of orders which have been subjected to the pulse compression processing.

* * * * *